US009364497B2

(12) United States Patent (10) Patent No.: US 9,364,497 B2
Smith et al. (45) Date of Patent: Jun. 14, 2016

(54) TREATMENT OF COGNITIVE DISORDERS

(75) Inventors: Anthony David Smith, Oxford (GB); Helga Margareta Refsum, Oxford (GB)

(73) Assignee: Isis Innovation Limited, Oxford, Oxfordshire (GB)

( * ) Notice: Subject to any disclaimer, the term of this patent is extended or adjusted under 35 U.S.C. 154(b) by 0 days.

(21) Appl. No.: 13/807,917

(22) PCT Filed: Sep. 17, 2010

(86) PCT No.: PCT/GB2010/051557
§ 371 (c)(1),
(2), (4) Date: Feb. 7, 2013

(87) PCT Pub. No.: WO2012/001336
PCT Pub. Date: Jan. 5, 2012

(65) Prior Publication Data
US 2013/0142769 A1 Jun. 6, 2013

Related U.S. Application Data

(60) Provisional application No. 61/360,759, filed on Jul. 1, 2010.

(51) Int. Cl.
*A61K 31/714* (2006.01)
*A61K 31/198* (2006.01)
*A61K 45/06* (2006.01)
*A61K 31/14* (2006.01)
*A61K 31/205* (2006.01)
*A61K 31/519* (2006.01)
*A61K 31/4415* (2006.01)
*G01N 33/68* (2006.01)

(52) U.S. Cl.
CPC ............... *A61K 31/714* (2013.01); *A61K 31/14* (2013.01); *A61K 31/198* (2013.01); *A61K 31/205* (2013.01); *A61K 31/4415* (2013.01); *A61K 31/519* (2013.01); *A61K 45/06* (2013.01); *G01N 33/6896* (2013.01)

(58) Field of Classification Search
CPC . A61K 31/14; A61K 31/205; A61K 31/4415; A61K 31/519; A61K 31/198; A61K 45/06; A61K 31/714; A61K 2300/00
USPC ........................................... 424/94.1; 514/52
See application file for complete search history.

(56) References Cited

U.S. PATENT DOCUMENTS

| 6,008,221 | A | 12/1999 | Smith et al. |
| 6,127,370 | A | 10/2000 | Smith et al. |
| 2007/0248696 | A1 | 10/2007 | Maletto et al. |
| 2009/0143433 | A1* | 6/2009 | Hendrix .................. A61K 9/06 514/321 |

FOREIGN PATENT DOCUMENTS

| JP | 2004-526793 A | 9/2004 |
| WO | WO 02/087593 A1 | 11/2002 |
| WO | WO 03/004039 A2 | 1/2003 |
| WO | WO 2007/127773 A2 | 11/2007 |
| WO | WO 2010/065162 A1 | 6/2010 |

OTHER PUBLICATIONS

Lehmann et al. (2003). Vitamin B12-B6-folate treatment improves blood-brain barrier function in patients with hyperhomocysteinaemia and mild cognitive impariment. Dementia and Cognitive Disorders, v16(3), p. 145-150.*
Boyle et al. (2006). Mild cognitive impairment: risk of Alzheimer disease and rate of cognitive decline. Neurology, v67, 441-445.*
McCaddon (2006). Homocysteine and cognitive impairment; as case series in a general practice setting Nutrition Journal, v5(6), 6 pages.*
Venn et al. (2003). Comparison of the effect of low-dose supplementation with L-5-methyltetrahydrofolate or folic acid on plasma homocysteine: a randomized placebo-controlled study. Am J Clin Nutr 2003, v77, p. 658-662.*
Lehmann, et al., "Vitamin $B_{12}$-$B_6$-Folate Treatment Improves Blood-Brain Barrier Function in Patients with Hyperhomocysteinaemia and Mild Cognitive Impairment." Dementia and Geriatric Disorders, vol. 16, No. 3; pp. 145-150 (2003).
Smith, et al., "Homocysteine-Lowering by B Vitamin Slows Rate of Accelerated Brain Atrophy in Mild Cognitive Impairment: A Randomized Controlled Trial", Public Library of Science, San Francisco, CA, vol. 5, No. 9 (Sep. 1, 2001).
Van Uffelen, et al., "Walking or Vitamin B for cognition in older adults with mild cognitive impairments? A randomised controlled trial" British Journal of Sports Medicine, vol. 42, No. 5; pp. 344-351 (May 2008).
Zhou, et al., "Acceleration of brain amyloidsis in a Alzheimers disease mouse model by a folate, vitamin B6 and B12 deficient diet", Experimental Gerontology, vol. 45, No. 3 (Mar. 1, 2010).
Balk, Ethan M., "Vitamin B6, B12, and Folic Acid Supplementation and Cognitive Function: A Systematic Review of Randomized Trials," American Med. Assoc., Arch Intern Med, vol. 167, (2007), downloaded form https://archinte.jamanetwork.com.
McCaddone, Andrew, "Homocysteine and Cognitive Impairment; a Case Series in a Genral Practice Setting," Nutrition Journal, vol. 5, No. 6., (2006) http://www.nutritionj.com/content/5/1/6.
Further Examination Report dated Jan. 30, 2014, New Zealand Application No. 606433, "Treatment of Cognitive Disorders", Application: Isis Innovation Limited.
Aisen, et al., "Treatment for MCI is the Evidence Sufficient" Neurology, vol. 70:2020-21 (2008).
Aisen, et al., "High-Dose B Vitamin Supplementation and Cognitive Decline in Alzheimer Disease", JAMA, :vol. 300 No. 15: 1774-83 (2008).
Anstey, et al., "Weekly Alcohol Comsumption, Brain Atrophy, and White Matter Hyperintensities in Community-Based Sample Aged 60-64", Psychosomatic Medicine, vol. 68:778-775 (2006).

(Continued)

*Primary Examiner* — Scott Long
*Assistant Examiner* — Sean C Barron
(74) *Attorney, Agent, or Firm* — Myers Bigel & Sibley, P.A.

(57) ABSTRACT

The invention relates to treatments of cognitive disorders e.g. Mild Cognitive Disorder comprising the use of agents which are capable of lowering homocysteine levels in a subject, preferably a human subject. Aspects of the invention relate to a method of treating such disorders comprising administering one or more B vitamins e.g. folic acid, Vitamin $B_6$ and/or Vitamin $B_{12}$ or derivatives thereof.

42 Claims, 10 Drawing Sheets

(56) References Cited

OTHER PUBLICATIONS

Antoniades, et al., "MTHFR 677 C>T Polymorphism Reveals Functional Importance for 5-Methylterahydrofolate, Not Homocysteine, in Regulation of Vascular Redox State and Endothelial Function in Atherosclerosis", Circulations, vol. 109:2507-2515 (2009).

Bleie, et al., "Changes in Basal and Postmethionine Load Concentration of Total Homocysteine and Cystathionine after B Vitamin Intervention", Am J Clin. Nutr., vol. 80:641-8 (2004).

Bradley, et al., "Serial Brain MRI at 3-6 Month Intervals as a Surrogate Marker for Alzheimer's Disease", Br J Radiol, vol. 75:506-513 (2002).

Brandt, et al., "Hereditary Influences on Cognitive Functioning in Older Men", Arch Neurol, vol. 50:599-603 (2002).

Brandt, et al., "The Hopkins Verbal Learning Test: Development of a New Memory Test with Six Equivalent Forms", Clinical Neuropsychologist, vol. 5:125-42 (1993).

Budge, et al., "Plasma Total Homocysteine and Cognitive Performance in a Volunteer Elderly Population", Ann NY Acad Sci, vol. 903:407-10 (2000).

Carlson, et al., "Trajectories of Brain Loss in Aging and the Development of Cognitive Impairment", Neurology, vol. 70: 828-33 (2008).

Clarke, et al., "Folate, Vitamin $B_{12}$, and Serum Total Homocysteine Levels in Confirmed Alzheimer Disease", Arch Neurol, vol. 55:1449-55 (Nov. 1998).

Clarke, et al. "Homocysteine-lowering Vitamin B Supplements do not Improve Cognitive Performance in Healthy Older Adults After Two Years", N Eng J Med, vol. 354:2764-72 (2007).

Clarke, et al., "B Vitamin for Prevention of Cognitive Decline", JAMA, vol. 300, No. 15:181-921 (2008).

DeCarli, "Mild Cognitive, Impairment: Prevalence, Prognosis, Aetiology, and Treatment", Neurology, vol. 2:15-21 (2003).

De Jager, et al., "Utility of TICS-M for the Assessment of Cognitive Function in Older Adults", Int J Geriatr Psychiatry, vol. 18: 316-24 (2003).

den Heijer, et al., "Type 2 Diabetes and Atrophy of Medial Temporal Lobes Structures on Brain MRI", Diabetologia, vol. 46: 1604-1610 (2003).

Durga, et al., "Effect of 3-year Folic Acid Supplementation on Cognitive Function in Older Adults in the FACIT Trail: a Randomisded, Double Blind, Controlled Trial", Lancet, vol. 369:208-16 (Jan. 20, 2007).

Elias, et al., "Homoxcysteine, Folate, and Vitamin $B_6$ and $B_{12}$ Blood Levels in Relation to Cognitive Performance: The Maine-Syracuse Study" Psychosom Med, vol. 68:547-54 (2006).

Enzinger, et al., "Risk Factor for Progression of Brain Atrophy in Aging: a Six-year Follow-up of Normal Subjects", Neurology, vol. 64:1704-11 (2005).

Erickson, et al., "Greater Intake of Vitamins B6 and B12 Spare Gray Matter in Healthy Elders: a Novel-based Morphometry Study", Brain Res, vol. 1199:20-26 (2008).

Eussen, et al., "Effect of Oral Vitamin B-12 with or without Folic Acid on Cognitive Function in Older People with Mild Vitamin B-12 Deficiency: a Randomized, Placebo-Controlled Trial", Am J Clin Nutr, vol. 84:361-70 (2006).

Folstein, et al., "Mini-Mental State' a Practical Method for Grading the Cognitive State of Patients for the Clinicians", J Psychiat Res., vol. 12:189-198 (1975).

Fox, et al., "Correlation Between Rates of Brain Atrophy and Cognitive Decline in AD", Neurology, Vo. 52:1687-1689 (1999).

Homocysteine Lowering Trialists' Collaboration, "Dose-Dependent Effects of Folic Acid on Blood Concentrations of Homocysteine: a Meta-Analysis of the Randomized Trials", Am J Clin Nutr, vol. 82:806-12 (2005).

Jack, et al., "Comparison or Different MRI Brain Atrophy Rate Measure with Clinical Disease Progression in AD", Neurology, vol. 62:591-600 (2004).

Jack, et al., "Brain Atrophy Rates Predict Subsequent Clinical Conversion in Normal Elderly and Amnestic MCI", Neurology, vol. 65:1227-1231 (2005).

Jorm, et al., "The Informant Questionnaire on Cognitive Decline in the Elderly (IQCODE): Socio-Demographic Correlates, Reliability, Validity and Some Norms", Psychol Med, vol. 19:1015-1022 (1989).

Killiany, et al., "Use of Structural Magnetic Resonance Imaging to Predict who will get Alzheimer's Disease", Ann Neurol, vol. 47:430-439 (2000).

McCaddon, et al., "Total Serum Homocysteine in Senile Dementia of Alzheimer Type", Int J Geriatr Psychiatry, vol. 13:235-239 (1998).

Nurk, et al., "Plasma Total Homocysteine and Memory in the Elderly: The Hordaland Homocysteine Study", Ann Neurol, vol. 58:847-857 (2005).

Petersen, et al., "Mild Cognitive Impairment 13 Ten Years Later", Neurol. vol. 66:1447-55 (2009).

Petersen, et al., "Mild Cognitive Impairment—Clinical Characterization and Outcome" Arch Neurol., vol. 56:303-308 (1999).

Pfeiffer, et al., "Trends in Circulating Concentrations of Total Homocystein among US Adolescents and Adults: Findings from the 1991-1994 and 1999-2004 National Health and Nutrition Examination Surveys", Cli Chem. vol. 54:801-813 (2008).

Plassman, et al., "Prevalence of Cognitive Impairment without Dementia in the United States", Ann Intern Med., vol. 148:427-34 (2008).

Refsum, et al., "The Hordaland Homocysteine Study: A Community Based Study of Homocysteine, its Determinants, and Association with Disease", American Society for Nutrition, vol. 136:1731S-40S (2006).

Refsum, et al., "Homocysteine, B Vitamins, and Cardiovascular Disease", N Engl J Med, vol. 335:207 (2006).

Refsum, et al., "Holotranscobalamin and Total Transcobalamin in Human Plasma: Determination, Determinants, and Reference Values in Healthy Adults", Clin Chem, vol. 52:129-37 (2006).

Resnick, et al., "Longitudinal Magnetic Resonance Imaging Studies of Older Adults: a Shrinking Brain", J Neurosci. vol. 23 No. 8:3295-3301 (2003).

Ries, et al., "Magnetic Resonance Imaging Characterization of Brian Structure and Function in Mild Cognitive Impairments: a Review" J Am Geriatr Soc. vol. 56:920-934 (2008).

Risacher, et al., "Baseline MRI Predictors of Conversion from MCI to Probable AD in the ADNI Cohort", Curr Alzheimer Res, vol. 6:347-361 (2009).

Sachdev, et al., "Relationship between Plasma Homocysteine Levels and Brain Atrophy in Healthy Elderly Individuals", Neurology, vol. 58:1539-41 (2002).

Seshadri, "Elevated Plasma Homocysteine Levels: Risk Factor or Risk Marker for the Development of Dementia and Alzheimer's Disease", J Alzheimer's Dis, vol. 9:393-398 (2006).

Seshadri,, et al., "Association of Plasma Total Homocysteine Levels with Subclinical Brain Injury", Arch Neurol, vol. 65:642-49 (2009).

Skoog, et al., "A Population-Based Study on Blood Pressure and Brain Atrophy in 85-Year-Olds" Hypertension, vol. 32:404-09 (1998).

Sluimer, et al., "Whole-Brain Atrophy Rate in Alzheimer Disease", Radiology, vol. 248:590-98 (2008).

Sotang, et al., "Protein Phosphate 2A Methyltransferse Links Homocysteine Metabolism with Tau and Amyloid Precursor Protein Regulation", Journal of Neuroscience, vol. 27(11):2751-2759 (Mar. 14, 2007).

Smith, "Imaging the Progression of Alzheimer Pathology Through the Brain", PNAS, vol. 99(7):4135-4137 (Apr. 2, 2002).

Smith, et al., "Vitamin B-12 and Cognition in the Elderly", Am J Cli Nutr., vol. 89(Suppl.):707S-11S (2009).

Smith, "The Worldwide Challenge of the Dementias: A Role for B Vitamins and Homocysteine?", Food and Nutrition Bulletin, vol. 29(2):S143-S172.

Smith, et al., "Accurate, Robust and Automated Longitudinal and Cross-Sectional Brain Change Analysis", NeuroImage, vol. 17:479-489 (2002).

Refusm, et al., "Vitamin $B_{12}$ status and rate of Brain Volume Loss in Community-dwelling elderly" Neurology, vol. 71:826-832 (2008).

Warden, et al., "Detection of Single-Nucleotide Polymorphisms by PCR with Universal Energy Transfer-Labeled Primers: Application of Folate- and Cobalamin-Related Genes" Clinical Chemistry, vol. 5(9):1713-1716 (2005).

(56) References Cited

OTHER PUBLICATIONS

Wedderburn, et al., "The Utility of Cambridge Behavioral Inventory in Neurodegenerative Disease", J. Neurol Neurosurg Psychiatry, vol. 79:500-5003 (2008).

Williams, et al, "Minimal Hippocampal Width Relates to Plasma Homocysteine in Community-Dwelling Older People", Age and Aging, vol. 31:440-444 (2002).

Wolters, et al., "Cognitive Performance in Relation to Vitamin Status in Healthy Elderly German Women—The Effects of 6-moths multivitamin supplementation", Preventive Medicine, vol. 31:253-259 (2005).

Yang, et al., "Correlations Between Folate, $B_{12}$, Homocysteine Levels, and Radiological Makers of Neuropathology in Elderly Post-Stroke Patients", Journal of the American College of Nutrition, vol. 26(3):272-278(2007).

Zylberstein, et al., "Midlife Homocysteine and late life Dementia in Woman a Prospective Population Study", Neurobiology of Aging, 1-7 (2009).

Den Heijer, T. et al., "Homocysteine anda Brain Atrophy on MRI of Non-Demented Elderly", Brain, vol., 126, p. 170-175 (2003).

Durga, Jane, et al., "Effect of 3-Year Folic Acid Supplementation on Cognitive Function in Older Adults in the FACIOT Trial: a Randomised, Double Blind, Controlled Trial", The Lancet, vol. 369, No. 9557, p. 208-216, (2007).

Lee, B-J, et al., "Folic Acid and Vitamin $B_{12}$ are more Effective than Vitamin $B_6$ in Lowering Fasting Plasma Homocysteine Concentration in Patients with Coronary Artery Disease", Euro. J. of Clnical Nutrition, vol. 58, p. 481-487 (2004.).

McKinley, Michelle C., et al., "Low-Dose vitamin B-6 Effectively Lowers Fasting Plasma Homocysteine in Healthy Elderly Prsons who are Folate and Riboflavin Replete", The Am. J. of Clinical Nutrition, vol. 73, No. 4, p. 759-764 (2001).

Miller, Alan, "The Methionine-Homocysteine Cycle and its Effects on Cognitive Diseases", Alternative Medicine Review, vol. 8, No. 1, p. 7-19 (2003.).

Weinstein, Andrea M., et al., "Treatment Practices of Mild Cognitive Impairment in California Alzheimer's Disease Centers", JAGS, vol. 57, issue 4, p. 686-690 (2009).

\* cited by examiner

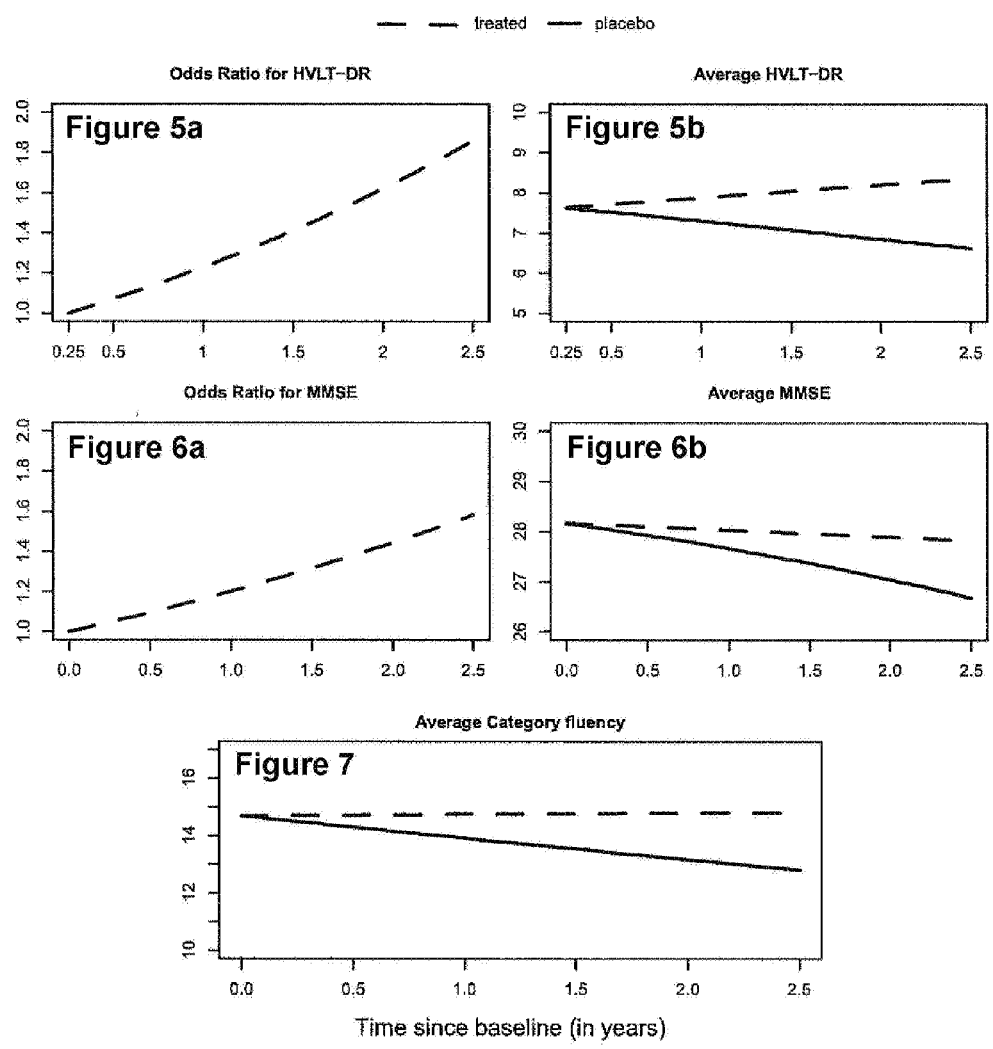

TREATMENT OF COGNITIVE DISORDERS

This invention relates to the treatment of cognitive disorders such as Mild Cognitive Impairment (MCI), a term given to a disorder which is typically characterised by a degree of cognitive impairment that does not affect daily life significantly. The invention relates at least in part to the use of one or more B vitamins, or other treatments, to lower concentrations of plasma total homocysteine in order to treat and/or reduce the progression of MCI and/or other types of cognitive impairment.

BACKGROUND

Cognitive ability may decline as a normal consequence of aging. Moreover, a significant population of elderly adults experiences a decline in cognitive ability that exceeds what is typical in normal aging. Mild Cognitive Impairment (MCI) reflects a degree of cognitive impairment without dementia that does not interfere with the activities of daily living. It is thought to be a prodromal state for Alzheimer's disease (De Carli, 2003; Petersen et al., 2009; Petersen et al., 1999). The prevalence of MCI is between 14% and 18% in those over 70 years old (Petersen et al., 2009; Plassman et al., 2008), which means that about 5 million people in the USA and 14 million in greater Europe suffer from this condition. Approximately half of those with MCI convert to Alzheimer's disease or to another form of dementia within 5 years (DeCarli, 2003) and thus there is an urgent need to identify treatments that will slow down or prevent this conversion. So far, no trial has been successful and currently there is no approved treatment for MCI.

In cognitively healthy elderly, the brain shows significant progressive atrophy (Resnick et al., 2003) and a much increased rate of brain atrophy is associated with the conversion from normal ageing to Alzheimer's disease (Bradley et al., 2002; Fox et al., 1999; Jack et al., 2004; Smith, 2002). An intermediate rate of atrophy is found in MCI (Carlson et al., 2008; Jack et al., 2005; Killiany et al., 2000; Ries et al., 2008; Risacher et al., 2009; Sluimer et al., 2008). Since the rate of brain atrophy is more rapid in subjects with MCI who convert to Alzheimer's disease (Jack et al., 2004), it is important to identify factors that determine the rate of atrophy since reducing the rate of atrophy might slow the conversion to Alzheimer's disease. One such factor appears to be raised concentrations of plasma total homocysteine (tHcy). Moderately elevated concentrations of tHcy have been associated with an increased risk of dementia, notably Alzheimer's disease, in many cross-sectional and prospective studies (Clarke et al., 1998; McCaddon et al., 1998; Seshadri, 2006; Smith, 2008; Zylberstein et al., 2009). Raised tHcy is also associated with both regional and whole brain atrophy, not only in Alzheimer's disease (Clarke et al., 1998) but also in normal elderly (den Heijer et al., 2003a; Sachdev et al., 2002; Seshadri et al., 2008; Williams et al., 2002; Yang et al., 2007). Thus, there remains a requirement to identify new treatments for the treatment of MCI that may act to retard brain atrophy in a subject and lowering tHcy levels could be one possible approach.

Despite the reported link between MCI and Alzheimer's Disease, it has been shown that it does not necessarily follow that treatments authorised for the treatment of Alzheimer's Disease have an effect on MCI patients. For example, clinical trials have been carried out on whether the Alzheimer's drug, galantamine, can be used as a treatment of MCI. These trials did not find any significant benefit for galantamine in improving function or preventing transition to Alzheimer's. However, investigators did note a significantly greater number of deaths in the galantamine treatment groups than in those receiving the placebo. (Winblad B, Gauthier S, Scinto L, Feldman H, Wilcock G K, et al. (2008) Safety and efficacy of galantamine in subjects with mild cognitive impairment. Neurology 70: 2024-2035.)

Clinical trials have also been carried out to determine whether rivastigmine (Exelon®) delayed the transition from MCI to Alzheimer's Disease. The trials found no significant benefit of rivastigmine on the progression rate to Alzheimer's Disease nor on cognitive function over four years. (Feldman H H, Ferris S, Winblad B, Sfikas N, Mancione L, et al. (2007) Effect of rivastigmine on delay to diagnosis of Alzheimer's disease from mild cognitive impairment: the InDDEx study. Lancet Neurol 6: 501-512.)

Thus, clinical trials have indicated that medicaments authorised for Alzheimer's Disease do not necessarily have any therapeutic effect on MCI or a conversion between MCI and Alzheimer's Disease.

BRIEF SUMMARY OF THE DISCLOSURE

In the broadest aspect, the present invention relates to treatment of cognitive disorders other than Alzheimer's by the administration of an agent which lowers homocysteine (tHcy) level in a subject. In one aspect, the agent may comprise one or more B vitamins. Embodiments of the invention may have utility in the treatment of cognitive disorders, e.g. Mild Cognitive Impairment (MCI), in a subject.

Thus, in accordance with the present invention, there is provided a method for treating mild cognitive impairment (MCI) in a subject comprising administering a therapeutically effective amount of at least one agent which lowers tHcy levels to the subject.

In one aspect of the invention, there is provided a method for treating i.e. retarding or preventing the onset and/or development of MCI in a subject comprising administering a therapeutically effective amount of at least one agent which lowers tHcy levels to the subject. The subject may or may not be suffering from MCI when treatment is commenced.

In one aspect of the invention, there is provided a method of improving cognitive function in a subject who suffers from or is believed to suffer from MCI comprising administering a therapeutically effective amount of at least one agent which lowers tHcy levels to the subject.

In one aspect of the invention, there is provided a method for delaying or preventing the development of Alzheimer's disease in a subject who suffers from MCI comprising administering a therapeutically effective amount of at least one agent which lowers tHcy levels to the subject.

In one aspect of the invention, there is provided a method for reducing the rate of brain atrophy in a subject comprising administering a therapeutically effective amount of at least one agent which lowers tHcy levels to the subject.

In one embodiment, the subject is a human and may be at least 60 years old e.g. is at least 70 years old.

In one embodiment, the method(s) of the invention comprise administering at least one B vitamin or derivative thereof to the subject. In one embodiment, the method(s) comprise administering a therapeutically effective amount of two B vitamins or derivatives thereof to the subject. In one embodiment, the method(s) of the invention comprise administering therapeutically effective amounts of three or more B vitamins or derivatives thereof. The first, second and/or third B vitamin each may be in the form of a salt or free acid.

In one embodiment, the method(s) of the invention comprise administering at least three B vitamins to the subject.

The first, second and third B vitamins may be independently selected from folic acid, Vitamin $B_6$ and Vitamin $B_{12}$ and derivatives thereof. Thus, the first B vitamin may be selected from folic acid, Vitamin $B_6$ and Vitamin $B_{12}$ and derivatives thereof. Furthermore, the second B vitamin may be selected from folic acid, Vitamin $B_6$ and Vitamin $B_{12}$ and derivatives thereof. Additionally, the third B vitamin may be selected from folic acid, Vitamin $B_6$ and Vitamin $B_{12}$ and derivatives thereof.

In one embodiment, the first B vitamin, the second B vitamin and the third B vitamin are each independently selected from the group consisting of folic acid (pteroylmonoglutamate), one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon units at various levels of oxidation, or a combination of two or more thereof.

In one embodiment, the first, second and third B vitamin(s) are independently selected from dihydrofolate, tetrahydrofolate, 5-methyltetrahydrofolate, 5,10-methylenetetrahydrofolate, 5,10-methenyltetrahydrofolate, 5,10-formiminotetrahydrofolate, 5-formyltetrahydrofolate (leucovorin) and 10-formyltetrahydrofolate.

In one embodiment, the method(s) of the invention comprise the simultaneous, separate or sequential administration of the first, second and third B vitamins. In one embodiment, the method(s) of the invention comprise administering a combination of folic acid, Vitamin $B_6$ and Vitamin $B_{12}$ to the subject. In one embodiment, the agent is selected from choline and betaine. Thus, in one embodiment, the agent is choline. In an alternative embodiment the agent is betaine.

In one embodiment, the method(s) of the invention comprise administering a therapeutically effective amount of betaine and/or choline in combination with at least one B vitamin. In one embodiment, the method(s) of the invention comprise administering a therapeutically effective amount of betaine and/or choline in combination with folic acid, Vitamin $B_6$ and Vitamin $B_{12}$ to the subject.

Embodiments of the methods described herein may result in the improvement of attention in the subject following administration of the at least one agent. Alternatively, or in addition, executive function and/or reaction time and/or learning or memory may be improved in the subject following administration of the at least one agent. The administration may be over a period of days, weeks, months or years.

The subject may have baseline levels of tHcy which exceeds 9.5 μmol/L.

In an embodiment, the method(s) of the invention comprise administering folic acid or a derivative thereof to the subject in a dosage form which comprises approximately 0.1 mg to 10 mg of said folic acid or derivative thereof e.g. approximately between about 0.5 mg to 1.5 mg and optionally about 0.8 mg of said folic acid or derivative thereof.

In an embodiment, the method(s) of the invention comprise administering Vitamin $B_{12}$ or a derivative thereof to the subject in a dosage form which comprises approximately from 0.01 mg to 2 mg of said Vitamin $B_{12}$ or derivative thereof e.g. from 0.4 mg to 1.0 mg, for example approximately 0.5 mg of said Vitamin $B_{12}$ or derivative thereof. The Vitamin $B_{12}$ may be for administration alone or in combination with other agents e.g. folic acid (or derivatives thereof), and other agents described herein.

In an embodiment, the method(s) of the invention comprise administering Vitamin $B_6$ or a derivative thereof to the subject in a dosage form which comprises approximately 1 mg to 40 mg of said Vitamin $B_6$ or derivative thereof e.g. from approximately 15 mg to 30 mg e.g. approximately 20 mg of Vitamin $B_6$ or derivative thereof.

In an embodiment, the method(s) of the invention comprise administering choline and/or betaine to the subject in a dosage form which comprises approximately from 1 g to 6 g of said choline or betaine e.g. 1, 2, 3, 4, 5 or 6 g.

In one aspect of the invention, there is provided a composition comprising at least one agent which lowers homocysteine (tHcy) levels for use in the treatment of mild cognitive impairment (MCI) in a subject. Also included in the present invention is the use of at least one agent which lowers homocysteine (tHcy) levels in the manufacture of a medicament for the treatment of mild cognitive impairment (MCI) in a subject.

In one aspect of the invention, there is provided a composition comprising at least one agent which lowers homocysteine (tHcy) levels for use in retarding the onset and/or development of MCI in a subject. Also included in the present invention is the use of at least one agent which lowers homocysteine (tHcy) levels in the manufacture of a medicament for retarding the onset and/or development of MCI in a subject.

In one aspect of the invention, there is provided a composition comprising at least one agent which lowers homocysteine (tHcy) levels for use in improving cognitive function in a subject. Also included in the present invention is the use of at least one agent which lowers homocysteine (tHcy) levels in the manufacture of a medicament for improving function in a subject.

In one aspect of the invention, there is provided a composition comprising at least one agent which lowers homocysteine (tHcy) levels for use in delaying or preventing the development of Alzheimer's disease in a subject who suffers from MCI. Also included in the present invention is the use of at least one agent which lowers homocysteine (tHcy) levels in the manufacture of a medicament for delaying or preventing the development of Alzheimer's disease in a subject who suffers from MCI.

In one aspect of the invention, there is provided a composition comprising at least one agent which lowers homocysteine (tHcy) levels for use in reducing the rate of brain atrophy in a subject. Also included in the present invention is the use of at least one agent which lowers homocysteine (tHcy) levels in the manufacture of a medicament for reducing the rate of brain atrophy.

The composition(s) and/or medicaments of the invention may be for administration to a subject is at least 60 years old e.g. at least 70 years old.

In one embodiment, the composition and/or medicament comprises a first B vitamin or derivative thereof. Optionally, the composition and/or medicament further comprises a second B vitamin. In one embodiment, the composition further comprises a third B vitamin.

Thus, in one embodiment, the composition and/or medicament of the invention comprises at least three B vitamins.

In one embodiment, the first B vitamin, the second B vitamin and the third B vitamin are independently selected from folic acid, Vitamin $B_6$ and Vitamin $B_{12}$ and derivatives thereof.

In one embodiment, the first B vitamin, the second B vitamin and the third B vitamin are each independently selected from the group consisting of folic acid (pteroylmonoglutamate), one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon units at various levels of oxidation, or a combination of two or more thereof.

In one embodiment, the first, second and third B vitamin(s) are independently selected from dihydrofolate, tetrahydrofolate, 5-methyltetrahydrofolate, 5,10-methylenetetrahydrofolate, 5,10-methenyltetrahydrofolate, 5,10-formiminotetrahydrofolate, 5-formyltetrahydrofolate (leucovorin) and 10-formyltetrahydrofolate.

In one embodiment, the composition and/or medicament of the invention comprises a combination of folic acid, Vitamin $B_6$ and Vitamin $B_{12}$.

In one embodiment, the composition and/or medicament comprises an agent selected from choline and betaine. In one embodiment, the agent is betaine. In one embodiment, the agent the agent is choline. In one embodiment, the composition and/or medicament comprises a therapeutically effective amount of betaine and/or choline in combination with a therapeutically effective amount of at least one B vitamin. In one embodiment, the composition comprises betaine and/or choline in combination with folic acid, Vitamin $B_6$ and/or Vitamin $B_{12}$.

The composition and/or medicament may be for use to (a) improve attention; (b) improve executive function; (c) improve reaction time; and/or (d) improve learning or memory in the subject.

The subject may comprise a baseline level of tHcy which is above about 9.5 µmol/L.

In one embodiment, the composition is a pharmaceutical composition and further comprises one or more pharmaceutically acceptable excipients. The composition may be for oral administration and is optionally is a solid dosage form.

In one embodiment, the composition and/or medicament comprises approximately 0.1 mg to 10 mg of folic acid or derivative thereof, e.g. approximately 0.5 mg to 1.5 mg of folic acid or derivative thereof, for example approximately 0.8 mg.

Alternatively or in addition, the composition and/or medicament between approximately 0.01 mg to 2 mg of Vitamin $B_{12}$ or derivative thereof e.g. between approximately 0.4 mg to 1.0 mg e.g. approximately 0.5 mg of the Vitamin $B_{12}$ or derivative thereof.

Alternatively or in addition, the composition and/or medicament may comprise between approximately 1 mg to 40 mg of Vitamin $B_6$ or derivative thereof e.g. between approximately 15 mg to 30 mg for example approximately 20 mg of the Vitamin $B_6$ or derivative thereof.

In one embodiment, the composition and/or medicament is for administration once a day. The composition may be for administration once a day for a period of weeks or months.

In one embodiment, the method comprises administering betaine either alone or in combination with other agents. In one embodiment, the method comprises administering betaine in combination with one or more B vitamins. In one embodiment, the method comprises administering choline either alone or in combination with other agents e.g. one or more B vitamins.

Embodiments of the invention may be dependent on the baseline level of tHcy in a subject. Thus, in one embodiment, the invention is for the treatment of MCI or other cognitive disorders in subjects which have baseline tHcy levels in the upper three quartiles. The invention encompasses treatment of MCI and other cognitive disorders in subjects which have a baseline tHcy above about 9.5 µmol/L.

The invention encompasses a method of reducing brain atrophy in classes of patients which have a tHcy concentration of above 9.5 µmol/L, comprising administering at least one B vitamin to the subject. The method may comprise administering at least one B vitamin selected from folic acid, Vitamin $B_6$ and Vitamin $B_{12}$ and derivatives thereof and combinations thereof. The method, in one embodiment, may comprise administering a combination of folic acid, Vitamin $B_{12}$ and Vitamin $B_6$ to a subject in need thereof. In one embodiment, the cognitive disorder is not Alzheimer's Disease.

Thus, embodiments of the present invention act by lowering tHcy concentrations via administration of high doses of supplementary B vitamins (e.g. folic acid, vitamins $B_6$ and $B_{12}$) to slow the rate of atrophy the brain of the elderly subjects with MCI. As described herein, embodiments of the invention are shown to lower tHcy levels by about 30% in populations from countries without mandatory folic acid fortification of flour.

BRIEF DESCRIPTION OF THE DRAWINGS

Embodiments of the invention are further described hereinafter with reference to the accompanying drawings, in which:

FIG. 5a is a graph showing the estimated odds ratio over time of correctly answering a question from the HVLT-DR for someone in the 'higher tHcy group' who has been treated compared to that same person if not treated. The odds ratio significantly increases over time. For example, the odds of a correct answer 2 years after starting the treatment for someone in the 'higher tHcy group' is 74% greater than his odds if no treatment was taken (P-value=0.004).

FIG. 5b is a graph showing how the estimated total HVLT-DR score changes over time in the 'higher tHcy group' for the average subject according to treatment status. Treatment resulted in maintenance of performance while the placebo group scores declined over time. For the HVLT-DR score, data was removed from the 0 month time-point to eliminate the initial practice effects.

FIG. 6a is a graph showing that the odds of a correct answer on the MMSE 2 years after starting the treatment for someone in the 'higher tHcy group' are 44% greater than if no treatment was taken (P-value=0.003).

FIG. 6b is a graph showing how the estimated total MMSE score changes over time in the 'higher tHcy group'. Those on placebo showed a decline in MMSE while those on treatment showed no significant change.

FIG. 7 gives the average Category fluency score over time for someone in the 'higher tHcy group' who has been treated compared to that same person if not treated. For example, the average number of words 2 years after starting the treatment for someone in the 'higher tHcy group' is 12% greater than his average number if no treatment was taken (P-value=0.003).

FIG. 9(c) shows the odds ratio of treatment versus placebo over two years.

DETAILED DESCRIPTION

Figure 1:
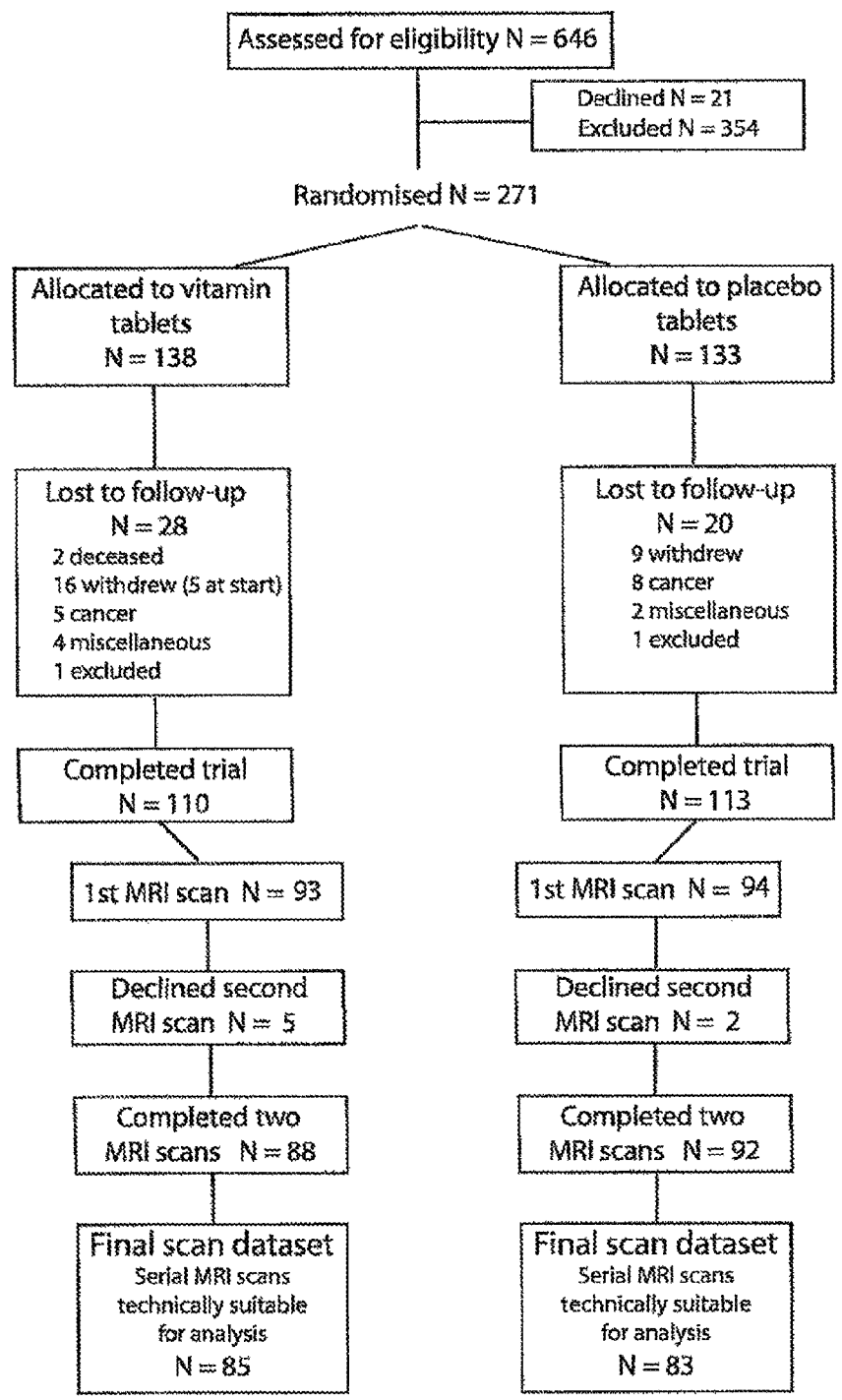
FIG. 1 is a graph showing the Participant Flow in a trial to study the effect of B vitamins on the rate of brain atrophy in MCI (example 1).

The invention is described in more detail below. Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopaedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Definitions and additional information known to one of skill in the art in immunology can be found, for example, in Fundamental Immunology, W. E. Paul, ed., fourth edition, Lippincott-Raven Publishers, 1999.

As used herein, the term "cognitive function" or "cognitive status" refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behaviour, and expressing an interest in one's surroundings and self-care. In one embodiment, the present invention results in improve memory. In humans, cognitive function may be measured, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG). See Folstein et al., J Psychiatric Res 12: 189-98, (1975); Robbins et al., Dementia 5: 266-81, (1994); Rey, L'examen clinique en psychologie, (1964); Kluger et al., J Geriatr Psychiatry Neurol 12: 168-79, (1999). In animal model systems, cognitive function may be measured in various conventional ways known in the art, including using a Morris Water Maze (MWM), Barnes circular maze, elevated radial arm maze, T maze or any other mazes in which the animals use spatial information. Other tests known in the art may also be used to assess cognitive function, such as novel object recognition and odour recognition tasks. Cognitive function may also be measured using imaging techniques such as Positron Emission Tomography (PET), functional magnetic resonance imaging (flvlRI), Single Photon Emission Computed Tomography (SPECT), or any other imaging technique that allows one to measure brain function. In animals, cognitive function may also be measured with electrophysiological techniques. Thus, in one embodiment, the present invention relates to the improvement of cognitive function of a subject. The subject may be an elderly subject e.g. over the age of 60, e.g. 70, 75 or 80 years of age.

As used herein, the term "Mild Cognitive Impairment" or "MCI" relates to a disorder or condition in which individuals have cognitive impairment beyond that expected for their age and education but which typically does not interfere with their daily activities. In some embodiments, the term "MCI" relates to a condition which may be considered a boundary or transitional stage between normal aging and dementia. MCI can present with a variety of cognitive symptoms including, for example, memory loss. Memory loss may be confirmed by for example; (a) the subject's report of his or her own memory impairment, which may be confirmed by another person; and/or (b) measurable, greater-than-normal memory impairment detected with standard memory assessment tests (Petersen R C, Roberts R O, Knopman D S, Boeve B F, Geda Y E, et al. (2009) Mild cognitive impairment: ten years later. Arch Neurol 66: 1447-1455). In one embodiment, the invention relates to the treatment or slowing of progression of MCI in a subject comprising the use of one or more B vitamins. The B vitamins for use in the present invention are described in more detail below. In one embodiment, the MCI may be amnestic MCI. In one embodiment, the subject does not suffer from other impairments of brain function, such as planning or attention. In an alternative embodiment, the subject has impairments of memory, language, or another mental function such that they suffer from (c) a decline in normal general thinking and reasoning skills and/or (d) a decline in a subject's ability to perform normal daily activities. Such impairments may be severe enough to be noticeable to other people and to show up on tests, but not serious enough to interfere with daily life. In one embodiment the individual is 50 years of age or greater e.g. 55, 60, 65, 70, 75, 80 or 85 years of age.

As used herein, "Age-Associate Memory Impairment (AAMI)" refers to a decline in memory due to aging. A patient or subject may be considered to have AAMI if he or she is at least 50 years old and meets all of the following criteria: a) The patient has noticed a decline in memory performance, b) The patient performs worse on a standard test of memory compared to young adults, c) All other obvious causes of memory decline, except normal aging, have been ruled out (in other words, the memory decline cannot be attributed to other causes such as a recent heart attack or head injury, depression, adverse reactions to medication, Alzheimer's disease, etc.). In one embodiment, the invention comprises the treatment of AAMI by the administration of at least one B vitamin as described herein.

As used herein, the term "Age-Related Cognitive Decline (ARCD)" refers to declines in memory and cognitive abilities that are a normal consequence of aging in humans (e.g., Craik & Salthouse, 1992). This is also true in virtually all mammalian species. In one embodiment, the invention comprises treating or reducing the rate of ARCD by administering an agent as described herein. In one embodiment, such a method comprises administering at least one B vitamin as described herein. In one embodiment, the method comprises administering a combination of folic acid, Vitamin $B_{12}$ and Vitamin $B_6$. Also encompassed by the present invention are compositions for use in treating ARCD comprising at least agent as described herein. In one embodiment, the composition comprises at least one B vitamin. In one embodiment, the composition comprises folic acid, Vitamin $B_{12}$ and Vitamin $B_6$.

As used herein, the terms "patient", "subject", or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats). In a preferred embodiment, the subject is a human.

As used herein, the terms "treatment" and "treating" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, diminishment of any direct or indirect pathological consequences of the disease, lowering the rate of disease progression, amelioration or palliation of the disease state, and remission or improved prognosis. A condition or subject refers to taking steps to obtain beneficial or desired results, including clinical results. Beneficial or desired clinical results include, but are not limited to, alleviation or amelioration of one or more symptoms associated with MCI, or age-related cognitive impairment, delay or slowing of that impairment, amelioration, palliation or stabilization of that impairment, and other beneficial results, such as improvement of cognitive function or a reduced rate of decline of cognitive function in subjects with age-related cognitive impairment or at risk thereof.

A "therapeutically effective amount" of a drug or agent, e.g. the Vitamin B(s) or derivatives thereof of the present invention, is an amount of a drug or an agent that, when administered to a subject will have the intended therapeutic effect, e.g. slowing of brain atrophy or improving cognitive function in a subject, e.g., a patient with MCI or a patient at risk thereof. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of the cognitive impairment, and the therapeutics or combination of therapeutics selected for administration, and the mode of administration. The skilled worker can readily determine the effective amount for a given situation by routine experimentation. In one embodiment, the at least one B vitamin as described herein are for administration on a daily frequency or more than once a day, e.g. 2, 3 or 4 times a day.

Agents

The present invention relates to the use of one or more agents which are capable of lowering homocysteine levels in a subject in need thereof. In one embodiment, the agent is choline or betaine. In one embodiment, the methods and compositions of the present invention comprise administering betaine at a dosage of from about 1 g to about 6 g per day, e.g. 1, 2, 3, 4, 5, or 6 g per day. The method may comprise administering betaine to the subject once a day or more. In one embodiment, the methods and compositions of the present invention comprise administering choline at a dosage of from about 1 g to about 6 g per day. The method may comprise administering choline to the subject once a day or more. In an alternative embodiment, the agent is N-acetyl-cysteine at a dosage of about 0.5 g to about 4 g per day.

The agents of the invention and methods which comprise the use of such agents may be for long term administration. That is to say, embodiments of the invention comprise administering the agents for a period of days, weeks, months or years. In one embodiment, the agents are for administration at least once a day for a month, 2, 3, 4, 5, 6, 7, 8, 9, 10, 11, 12, 13, 14, 15, 16, 17, 18, 19, 20, 21, 22, 23 or 24 months or more.

B Vitamins

In one embodiment, the agent is a B vitamin. Thus, the present invention involves the use of one or more B vitamins. In one embodiment, the first B vitamin is selected from Vitamin $B_6$, Vitamin $B_{12}$ and folic acid and derivatives thereof. In one embodiment, the composition is for use in combination with a composition comprising one or more alternative B vitamins.

In one embodiment, the methods, medicaments and/or compositions of the present invention may further comprise a second B vitamin. The second B vitamin may be selected from, folic acid, Vitamin $B_6$ and Vitamin $B_{12}$ and derivatives thereof.

In one embodiment, the method and compositions of the invention further comprise use of a third B Vitamin. In one embodiment, the third B vitamin is selected from Vitamin $B_6$, Vitamin $B_{12}$ and folic acid and derivatives thereof.

In one embodiment the methods and/or compositions of the present invention comprise use of a combination of three or more B vitamins, said combination comprising Vitamin $B_6$, Vitamin $B_{12}$, and folic acid or derivatives of one or more of the aforementioned Vitamins. Thus, the present invention includes the administration of a combination of B vitamins, either comprised in the same composition or administered separately. In one embodiment, there is provided a combination of B vitamins e.g. Vitamin $B_6$, Vitamin $B_{12}$, and folic acid or derivatives for use in the treatment of cognitive disorders, as described in more detail herein.

In one embodiment, the invention comprises administering folic acid (pteroylmonoglutamate) to a subject either alone or in combination with other agents described herein. Folic acid is also known as vitamin $B_9$ or folacin. In one embodiment, the method comprises administering a compound selected from folic acid (pteroylmonoglutamate), one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon units at various levels of oxidation, or a combination of two or more thereof. In one embodiment of the present invention, folic acid or folate in one of its forms described above may be present in a composition and/or administered to a subject in an amount ranging from about 0.1 mg to about 10 mg. In another embodiment, Vitamin $B_{12}$ may be present in the amount ranging from about 0.01 mg to about 1.5 mg. In another embodiment, Vitamin $B_{12}$ may be present in the amount ranging from about 0.4 mg to about 0.9 mg. In one embodiment of the present invention, Vitamin $B_{12}$ may be present in the amount of about 0.8 mg.

In one embodiment, the invention comprises administering Vitamin $B_{12}$ either alone or in combination with other B vitamins. Vitamin $B_{12}$ is also known as cobalamin and can be converted to the active coenzymes, methylcobalamin and 5'-deoxyadenosylcobalamin. These coenzymes are necessary for folic acid metabolism, removal of homocysteine, and myelin synthesis. For example, methylcobalamin catalyzes the demethylation of a folate cofactor. A lack of demethylation may result in deficiency of the folate from required for DNA synthesis. Deoxyadenosylcobalamin is the coenzyme for the conversion of methylmalonyl-CoA to succinyl-CoA, and is required for the entry of odd-chain fatty acids into the citric acid cycle. Vitamin $B_{12}$, along with pyridoxine and folic acid in implicated in the proper metabolism of homocysteine. Vitamin $B_{12}$ is available, for example, as cyanocobalamin, methylcobalamin, hydroxocobalamin and adenosylcobalamin.

One embodiment of the compositions and methods of the present invention may include Vitamin $B_{12}$. In one embodiment of the present invention, Vitamin $B_{12}$ may be present in a composition and/or administered to a subject in an amount ranging from about 0.01 mg to about 1.5 mg. In another embodiment, Vitamin $B_{12}$ may be present in the amount ranging from about 0.2 mg to about 1 mg. In another embodiment, Vitamin $B_{12}$ may be present in the amount ranging from about 0.4 mg to about 0.8 mg. In one embodiment of the present invention, Vitamin $B_{12}$ may be present in the amount of about 0.5 mg. In one embodiment, the Vitamin $B_{12}$ is cyanocobalamin.

In one embodiment, the invention comprises administering Vitamin $B_6$ either alone or in combination with other B vitamins. Vitamin $B_6$ may be present in a composition and/or administered to a subject in an amount ranging from about 0.5 mg to about 40 mg. In another embodiment, Vitamin $B_6$ may be present in the amount ranging from about 15 mg to about 30 mg. In another embodiment, Vitamin $B_6$ may be present in the amount ranging from about 15 mg to about 25 mg. In one embodiment of the present invention, Vitamin $B_{12}$ may be present in the amount of about 20 mg.

In one embodiment, choline is administered to a subject. Choline may be comprised in for example a phospholipid such as phosphatidylcholine. In one embodiment, betaine is administered to the subject. Choline is a pre-cursor to betaine in the human body. Betaine is a substrate which acts in the conversion of homocysteine to methionine.

Pharmaceutically Acceptable Carriers

The present invention includes pharmaceutical compositions as described herein. In one embodiment, the composition comprises a pharmaceutically acceptable carrier. The pharmaceutically acceptable carriers useful in the methods disclosed herein are conventional. Remington's Pharmaceutical Sciences, by E. W. Martin, Mack Publishing Co, Easton, Pa., 15th Edition (1975), describes compositions and formulations suitable for pharmaceutical delivery of the IL-2 receptor antagonists herein disclosed.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

In a preferred embodiment, the compositions of the invention are for oral administrations and are e.g. solid dosage forms. Solid dosage forms for oral administration include capsules, tablets, pills, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid, for example; b) binders such as carboxymethylcellulose, alginates, gelatin, polyvinylpyrrolidone, sucrose and acacia, for example; c) humectants such as glycerol, for example; d) disintegrating agents such as agar-agar, calcium carbonate, potato or tapioca starch, alginic acid, certain silicates and sodium carbonate, for example; e) solution retarding agents such as paraffin, for example; f) absorption accelerators such as quaternary ammonium compounds, for example; g) wetting agents such as cetyl alcohol and glycerol monostearate, for example; h) absorbents such as kaolin and bentonite clay for example and i) lubricants such as talc, calcium stearate, magnesium stearate, solid polyethylene glycols, sodium lauryl sulfate and mixtures thereof, for example. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

The compositions of the invention may be in the form of oral formulations, and consequently the methods of the invention comprise oral administration of the agents e.g. choline, betaine and/or B vitamin(s). Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, capsules, pills, and granules can be prepared with coatings and shells such as enteric coatings and other coatings such as multiple coatings, for example, well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions which can be used include polymeric substances and waxes.

Alternatively, the agents described herein e.g. B vitamin(s), betaine and/or choline may be comprised in a liquid dosage form. Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

In one embodiment, the mode of administration of the agent of the invention may be intravenous, inter-arterial, intramuscular or subcutaneous injection. In one embodiment, one or more B vitamins may be administered intramuscularly, e.g. Vitamin $B_{12}$. The B vitamins described herein may be for use in the same or in different compositions.

The invention is described further with reference to the following non-limiting examples:

EXAMPLE 1

Introduction

Raised concentrations of plasma total homocysteine (tHcy) are a risk factor for cognitive decline and Alzheimer's disease and are associated with more rapid atrophy of the brain. An increased rate of brain atrophy is characteristic of Mild Cognitive Impairment (MCI). The inventors carried out a randomised controlled trial (VITACOG, ISRCTN 94410159) to see if a tHcy-lowering therapy (high-dose folic acid, vitamins $B_6$ and $B_{12}$) will slow the rate of brain atrophy and therefore have therapeutic benefit in the treatment of MCI.

The subjects comprised 271 individuals (of 646 screened) with Mild Cognitive Impairment. A subset (187) volunteered to have cranial MRI scans at the start and finish of the study. The study took place between 2004 and 2009 at the Oxford Project to Investigate Memory and Ageing (OPTIMA), University of Oxford. Participants were randomly assigned to two groups of equal size, one treated with tablets containing folic acid (0.8 mg/d), vitamin $B_{12}$ (0.5 mg/d) and vitamin $B_6$ (20 mg/d), the other with a placebo tablet; treatment was for 24 months. The pre-specified main outcome measure was the change in the rate of atrophy of the whole brain. A total of 168 participants (85 in active treatment group; 83 receiving placebo) completed the MRI section of the trial. The mean rate of brain atrophy per year was 30% lower in the active treatment group than in the placebo group (0.76% [95% CI, 0.63-0.90] versus 1.08% [0.94 01.22]. P=0.001). The treatment response was related to baseline tHcy levels: the rate of atrophy in participants with tHcy >13 μmol/L was 53% lower in the active treatment group. The treatment response was also related to the change in plasma tHcy levels during the trial: those whose tHcy levels decreased the most had the lowest atrophy rate. The rate of atrophy was one of the factors influencing the final cognitive test scores: a greater rate of atrophy was related to a lower cognitive score. Thus, the present invention provides a method of slowing the accelerated rate of brain atrophy in Mild Cognitive Impairment by treatment with B vitamins.

Methods

Study Protocol

Participants in the Oxford area were recruited between April 2004 and November 2006 through advertisements in the local newspaper or radio seeking people ≥70 years old with concerns about their memory. Via a telephone interview, respondents completed a health screening questionnaire relating to inclusion and exclusion criteria, and completed the TICS-M and a category fluency test (CERAD) (De Jager et al., 2003; Morris et al., 1989). Eligible participants were asked if they would agree to have two cranial MRI scans, one at the start and one two years later at the end of the treatment, but it was emphasised that the scans were voluntary. The study was approved by a NHS research ethics committee (COREC 04/Q1604/100).

Inclusion criteria included: age above 70 y; subjective concern about memory; study partner available as informant; diagnosis of MCI according to Petersen's criteria with activities of daily living, an objective memory problem assessed with the TICS-M (Brandt et al., 1993) based on previously defined cut-off scores for MCI (De Jager et al., 2003), i.e. a score of 17-29 out of a maximum of 39. For borderline cases: if TICS-M was >29 but category fluency <19 or TICS-M word recall ≤10/20, subjects were eligible. Alternatively, if TICS-M was <17 but category fluency was <19 or TICS-M word recall ≤10/20, subjects were eligible. Other methods to confirm the MCI diagnosis collected at the first visit were an MMSE (Folstein et al., 1975) score of >24/30 and no evidence of dementia. Exclusion criteria included; a diagnosis of dementia or being treated with anti-dementia drugs; active cancer; major stroke within past 3 months; treatment with methotrexate, anti-cancer or anti-epileptic drugs, or taking folic acid >300 μg/d, pyridoxine >3 mg/d or cobalamin >1.5 μg/d by mouth or any dose by injection.

At the clinic visit, participants provided blood and urine samples and underwent a variety of cognitive tests, including the MMSE (Folstein et al., 1982) and completed the Geriatric Depression Scale (GDS) questionnaire (Yesavage et al. 1982). Participants also had a simple test of their vibration sense in the ankle with a tuning fork. Participants were contacted by telephone at the following times after starting treatment: 3, 6, 12, 15 and 18 months to check compliance, to ask about adverse events and to carry out a verbal memory test. After 24 months, participants returned to the clinic for examination and blood tests. The cognitive test battery was repeated as well. A final telephone assessment of adverse events and cognition was done at 27 months.

Subjects with MCI, by Petersen's revised criteria for amnestic and non-amnestic MCI (Petersen et al., 2009), and who also fulfilled entry criteria and gave written consent, were randomised to either a treatment group or a placebo group. Centralised telephone randomisation was used with full allocation concealment and minimisation for age, gender, baseline TICS-M score and consent for MRI. The treatment group received TrioBe Plus® (meda AB/Recip AB, Box 906, Pipers väg 2A, SE-170 09 Solna, Sweden) containing 0.8 folic acid, 0.5 mg cyanocobalamin and 20 mg pyridoxine HCl, or a placebo tablet. The placebo tablet was identical to the vitamin tablet (Triobe Plus®) except for omission of the vitamins and the addition of iron oxide and ferrous sulphate (0.0055%) to give a colour to match the vitamin tablet.

The treatment period was 2 years. Each participant received their study medication at first visit and by post at 6-monthly intervals. For those who consented to the MRI scans, the tablets were dispensed on the day of the first scan.

Blood Sampling and Assays

At baseline and after 2 yr, non-fasting blood samples were collected by venipuncture. Plasma tHcy, folate, cobalamin, holoTC, and total TC were determined as previously described. (Vogiatzoglou et al., 2008) TC saturation was calculated as a ratio of holoTC to total TC. Plasma cystathionine was determined by liquid chromatography tandem mass spectrometry. (Antoniades et al., 2009) Genomic DNA was extracted from blood using the Wizard DNA Purification Kit (Promega, Southampton, UK). The MTHFR 677C>T polymorphism (NCBI Entrez Gene 4524) and the TCN2 776C>G polymorphism (NCBI Entrez Gene 6948) were genotyped using the Ampliflour SNP Genotyping System (Chemicon, Watford, UK) (Warden and Refsum, 2005) while APOE genotypes (NCBI Entrez Gene: 348) was determined using a one-stage PCR method. (Wenham et al., 1991).

MRI Scans

Volumetric cranial MRI scans at baseline and after 2 y were carried out. Specifically cranial MRI scans were carried out on a 1.5T MRI system (Sonata; Siemens Medical Solutions, Erlangen, Germany). The protocol was T1-weighted acquisition, gradient echo (FLASH-Fast Low angle shot) 3D acquisition with 1 mm isotropic voxels Flip angle 19 degrees TR=12 ms TE 5.65 ms. 208 slices per slab with 1 slab acquired in coronal orientation, 1 average. This was repeated three times and averaged after acquisition and cross-repeat alignment.

A fully automated, quantitative method, SIENA, was used to derive the rate of whole brain atrophy per y. SIENA is accurate (around 0.2% brain volume change error) and achieves high robustness (Smith et al., 2002). A cross-sectional method (SIENAX) was used to estimate normalised brain volume from a single image, using the skull to normalise spatially, with respect to a standard image (Smith et al., 2002). A participant's normalised brain volume at baseline was used as a co-variate in some of the analyses.

The rate of change is estimated from two MR images taken at different time points. SIENA automatically segments brain from non-brain in each image, and estimates the external surface of the skull in each image. The two brain images are registered, while using the skull images to constrain scaling and skew; this corrects for changes in imaging geometry over time. Brain surface points (including ventricle surfaces) are found using the registered brain images to sub-voxel accuracy, and the surface motion estimated on the basis of these points. The mean perpendicular edge motion across the entire brain surface produces a change image and can be converted into estimates of rate of atrophy that reflect changes in both grey and white matter (Smith et al., 2002).

Statistical Analysis

Power calculations were based on existing data using the same MRI procedure and SIENA in 49 elderly with MCI from OPTIMA where the mean (SD) rate of shrinkage was 0.74 (0.27)% per year. To detect a 20% reduction in rate, 70 subjects per group were required for 90% power, or 50 subjects per group for 80% power at alpha=0.05 (two tailed). On the basis of a drop-out rate or failed MRI of ~20%, we aimed for a sample size of 90 in each arm at the start of the study.

The main outcome measure was to determine whether the rate of atrophy of the whole brain per year over the trial period differed between the treatment groups, using the SIENA method. Since the requirement was that subjects had both a baseline and a follow-up MRI, a per-protocol analysis was conducted for the main outcome. Subjects were initially analysed in the groups to which they were randomised. The data was also analysed according to biological compliance, defined by identifying subjects in each group that had taken B-vitamin supplements (or received cobalamin injections), using the following cut-off values: an increase from baseline to follow-up in plasma folate of >10 nmol/L and in cobalamin of >150 pmol/L. Age was considered a confounding variable for the primary endpoint (Bradley et al., 2002). A variety of other covariates that might be associated with rate of brain atrophy (Anstey et al., 2006; Den Jeijer et al., 2003b; Enzinger et al., 2005; Jack et al., 2004; Skoog et al., 1998; Vogiatzoglou et al., 2008) or with B vitamin status (Refsum et al., 2006) were identified before the study was analysed (listed in Table 2 below). The assessment of covariates included a univariate procedure (unpaired t test or Pearson's correlations), followed by age-adjusted analyses. If any variable was associated in the age-adjusted analysis at P<0.10, it was included in subsequent analysis. Differences between intervention groups were tested using the Chi square test for categorical variables and the t test or analysis of variance for continuous variables.

Pre-specified secondary analyses included cognitive and depression scores, serious adverse events, withdrawals, compliance and the changes in biochemical markers. Subgroup analyses using ANOVA (categorical variables) or linear regression (continuous variables) included the influence of baseline markers on treatment effect, the rate of atrophy in the two groups after evaluation of biochemical compliance, association between change in biochemical markers (independent of treatment code) and rate of atrophy, and rate of atrophy in relevant subgroups. Report P values are 2-sided and unadjusted for multiple comparisons; P<0.05 was regarded as statistically significant. SPSS for Macintosh ($16^{th}$ ed.) or Windows ($17^{th}$ ed.), SPSS Inc, Chicago, Ill.; USA) was used for the statistical analyses.

Results

Participants

The flow of participants through the study is shown in FIG. 1. From a total of 646 participants assessed through the initial telephone interview, 292 fulfilled the entry criteria. The numbers lost to follow-up were similar in both groups, with 110 and 113 completing the 24 month trial in the active group and placebo group respectively. The primary analysis included only those subjects where there was technically good MRI scans at baseline and at follow-up, i.e. 85 in the active group and 83 in the placebo. The baseline characteristics in the groups were similar (TABLE 1 and 2). The mean (SD) period between MRI scans was 24.3 (0.7) months.

Adherence and Biological Vitamin Response

Adherence, assessed by counting returned tablets, was good in both groups: overall more than 78% of participants used at least 75% of their medication. Adherence was also assessed by measuring plasma vitamin concentrations and related compounds (Table 2). In the active group, geometric mean (95% CI) of plasma folate increased by nearly 270% and plasma cobalamin doubled. In contrast, the corresponding changes for the placebo group were modest increases of 3% and 10% respectively. Plasma tHcy decreased by 22.5% in the active group, but increased by 7.7% in the placebo group. Using criteria for biological compliance based on changes in folate or cobalamin, as defined in Methods, it was found that 17 out of 83 (20.5%) of the placebo group had taken supplementary folic acid or cobalamin, whereas in the active group, 14 out of 84 subjects (16.7%) with blood samples available did not take, or did not absorb, the vitamins, at least in the period prior to the second blood sampling (at 24 months). Thus, altogether 136 subjects are defined as biologically compliant.

TABLE 1

Baseline characteristics of the participants

| Characteristics | Placebo group (n = 83) | | Active treatment group[a] (n = 85) | |
|---|---|---|---|---|
| | Mean or n | SD or % | Mean or n | SD or % |
| Age, y | 76.2 | 4.5 | 77.0 | 5.2 |
| Women, n (%) | 52 | 62.7 | 50 | 58.8 |
| Years of education | 14.8 | 3.5 | 14.3 | 3.6 |
| Body Mass Index, kg/m$^{2b}$ | 26.6 | 4.2 | 25.3 | 3.4 |
| Systolic blood pressure, mmHg | 147 | 19 | 148 | 25 |
| Diastolic blood pressure, mmHg | 80 | 11 | 80 | 11 |
| TICS-M score | 24.8 | 2.7 | 24.9 | 2.8 |
| MMSE score | 28.3 | 1.5 | 28.3 | 1.8 |
| Initial brain volume, mL | 1376 | 71 | 1387 | 86 |
| Depression score (GDS)[c] | 7.5 | 5.2 | 5.6 | 4.0 |
| Ever-smoker, n (%) | 43 | 51.8 | 38 | 44.7 |
| No ankle vibration sense, n (%) | 50 | 60.2 | 55 | 64.7 |
| Hemoglobin, g/L | 138.4 | 11.8 | 137.9 | 12.8 |
| MCV, fL | 93.0 | 4.3 | 92.3 | 4.4 |
| Creatinine, μnik/L | 97 | 17 | 96 | 18 |
| APOE ε4 positive, n (%) | 29 | 34.9 | 22 | 25.9 |
| MTHFR 677C > T allele frequency (%) | | 34.9 | | 34.7 |
| TCN2 776C > G allele frequency (%) | | 30.1 | | 37.1 |
| Use of B vitamins at baseline, n (%) | 17 | 20.5 | 14 | 16.5 |
| Use of fish-oils, omega-3, n (%) | 31 | 37.3 | 36 | 42.4 |
| Diabetes any time, n (%) | 10 | 12.05 | 4 | 4.7 |
| Use of CVD drugs baseline, n (%) | 36 | 43.4 | 42 | 49.4 |
| Use of centrally acting drugs, n (%) | 20 | 24.1 | 23 | 27.1 |
| Use of aspirin baseline (%) | 28 | 33.7 | 26 | 30.6 |
| Other NSAIDs baseline | 12 | 14.5 | 18 | 21.2 |
| Stroke, TIA, MRI intact at baseline | 15 | 18.1 | 13 | 15.3 |
| History of MI baseline | 6 | 7.3 | 6 | 7.1 |
| Alcohol consumption (units/week) | 7.2[d] | 8.6 | 8.2 | 9.3 |

Abbreviations:

APOE, gene for apoliprotein E;

CVD, cardiovascular disease;

GDS, Geriatric Depression Scale;

MCV, mean red cell volume;

MI, myocardial infarct;

MMSE, mini-mental state examination;

MTHFR, gene for methylenetetrahydrofolate reductase;

NSAID, non-steroidal anti-inflammatory drug;

TIA, transient ischemic attack;

TICS-M, telephone interview of cognitive status, modified

[a]Active treatment group received daily supplements of folic acid (0.8 mg), vitamin B$_{12}$ (0.5 mg) and vitamin B$_6$ (20 mg) for 24 months.

[b]P = 0.22;

[c]P = 0.009;

[d]Excluding one high outlier.

TABLE 2

Folate and cobalamin markers in plasma before and after 2 y of intervention

|  |  |  | Placebo group | | | Active treatment group[a] | | | P value[b] |
|---|---|---|---|---|---|---|---|---|---|
|  |  | N | Geometric mean | 95% C.I. | N | Geometric mean | 95% C.I. | |
| tHcy (μmol/L) | Before | 83 | 11.27 | (10.58-12.00) | 85 | 11.25 | (10.58-11.97) | 0.974 |
|  | After | 83 | 12.14 | (11.40-12.93) | 84 | 8.72 | (8.29-9.17) | <0.001 |
|  | P value[c] |  | <0.001 |  |  | <0.001 |  |  |
| Folate (nmol/L) | Before | 83 | 24.2 | (21.4-27.5) | 85 | 22.4 | (19.4-25.9) | 0.428 |
|  | After | 83 | 24.9 | (21.4-29.1) | 84 | 82.1 | (74.6-90.4) | <0.001 |
|  | P value[c] |  | 0.695 |  |  | <0.001 |  |  |
| Vitamin B$_{12}$ (pmol/L) | Before | 83 | 333 | (310-357) | 85 | 330 | (303-360) | 0.891 |
|  | After | 83 | 366 | (335-400) | 84 | 672 | (626-722) | <0.001 |
|  | P value[c] |  | 0.018 |  |  | <0.001 |  |  |
| HoloTC (pmol/L) | Before | 83 | 68 | (61-76) | 85 | 63 | (55-72) | 0.406 |
|  | After | 83 | 73 | (65-82) | 84 | 182 | (162-204) | <0.001 |
|  | P value[c] |  | 0.116 |  |  | <0.001 |  |  |
| TC saturation (%) | Before | 83 | 7.35 | (6.54-8.25) | 85 | 6.65 | (5.72-7.73) | 0.306 |
|  | After | 83 | 7.17 | (6.26-8.21) | 84 | 20.42 | (18.21-22.90) | <0.001 |
|  | P value[c] |  | 0.648 |  |  | <0.001 |  |  |
| Cystathionine (μmol/L) | Before | 83 | 0.303 | (0.273-0.337) | 85 | 0.265 | (0.237-0.295) | 0.082 |
|  | After | 83 | 0.350 | (0.311-0.395) | 84 | 0.215 | (0.196-0.235) | <0.001 |
|  | P value[c] |  | 0.002 |  |  | <0.001 |  |  |

Abbreviations:
HoloTC, holotranscobalamin;
TC saturation, ratio of holoTC to total TC;
tHcy, plasma total homocysteine
[a]Active treatment group received daily supplements of folic acid (0.8 mg), vitamin B$_{12}$ (0.5 mg) and vitamin B$_6$ (20 mg) for 24 months.
[b]Student's t-test for paired samples,
[c]Student's test for unpaired samples.

Factors Associated with Rate of Atrophy in Placebo Group

These factors are listed in Tables 3 and 4. Age was strongly associated with rate of brain atrophy (r=0.32, P<0.01) and so all subsequent analyses were adjusted for age. Neither sex, smoking, BMI, alcohol consumption, APOE4 nor MTHFR 677C>T polymorphism was associated with the rate of atrophy (P>0.1 for all, adjusted for age). For the continuous variables, rate of atrophy was significantly associated with baseline log tHcy (partial r=0.41, P<0.001) and with plasma creatinine (partial r=0.21, P=0.049). Borderline associations were observed for diastolic blood pressure (partial r=−0.21, P=0.054), and for initial brain volume (partial r=−0.19, P=0.092). The latter four variables were included in subsequent adjusted analyses.

TABLE 3

Pearson correlations with the rate of atrophy (% per year) in the placebo group (N = 83)

|  | Unadjusted | | Age-adjusted | |
|---|---|---|---|---|
|  | Correlation | P | Correlation | P |
| Age at first visit | 0.317 | 0.004 |  |  |
| Initial brain volume | −0.319 | 0.003 | −0.187 | 0.092 |
| Total schooling | 0.011 | 0.923 | 0.030 | 0.787 |
| Body mass index at baseline | 0.056 | 0.615 | 0.064 | 0.565 |
| Diastolic blood pressure at baseline | −0.310 | 0.004 | −0213 | 0.054 |
| Systolic blood pressure at baseline | −0.101 | 0.362 | −0.084 | 0.455 |
| Creatinine at baseline | 0.274 | 0.012 | 0.218 | 0.049 |
| Depression score (GDS) at baseline | 0.156 | 0.158 | 0.148 | 0.184 |
| Cystathionine at baseline | 0.101 | 0.363 | 0.102 | 0.362 |
| Log folate at baseline | −0.062 | 0.58 | −0.092 | 0.411 |
| Log vitamin B$_{12}$ baseline | −0.052 | 0.644 | −0.002 | 0.988 |
| Log holoTC at baseline | −0.183 | 0.098 | −0.125 | 0.264 |
| Log TCsaturation at baseline | −0.268 | 0.014 | −0.180 | 0.105 |
| Log tHcy at baseline | 0.492 | <0.001 | 0.407 | <0.001 |

Abbreviations:
GDS, Geriatric Depression Scale;
HoloTC, holotranscobalamin;
TCsaturation, ratio of holoTC to total TC;
tHcy, total homocysteine

TABLE 4

Subgroup analyses: effects of several factors on the rate of atrophy and on the treatment effect

| Factor | Placebo N | Atrophy rate (95 % CI) %/y | Active treatment[a] N | Atrophy rate (95 % CI) % y | P value[b] Treatment | Factor | Interaction |
|---|---|---|---|---|---|---|---|
| Age ≤75.00 years | 36 | 0.95 (0.74-1.17) | 39 | 0.64 (0.43-0.84) | 0.004 | 0.023 | 0.824 |
| Age >75.00 years | 47 | 1.16 (0.98-1.35) | 46 | 0.89 (0.70-1.08) | | | |
| Male | 31 | 1.04 (0.81-1.26) | 35 | 0.85 (0.64-1.07) | 0.004 | 0.707 | 0.267 |
| Female | 52 | 1.11 (0.94-1.29) | 50 | 0.70 (0.52-0.88) | | | |
| Amnestic MCI | 51 | 1.15 (0.97-1.33) | 46 | 0.87 (0.67-1.06) | 0.004 | 0.107 | 0.741 |
| Non-amnestic MCI | 26 | 1.00 (0.75-1.26) | 31 | 0.65 (0.42-0.88) | | | |
| Never smoker | 40 | 1.02 (0.82-1.23) | 47 | 0.75 (0.56-0.93) | 0.002 | 0.453 | 0.708 |
| Ever smoker | 43 | 1.14 (0.94-1.33) | 38 | 0.78 (0.58-0.99) | | | |
| No aspirin, baseline | 55 | 1.11 (0.94-1.27) | 59 | 0.66 (0.50-0.82) | 0.021 | 0.190 | 0.052 |
| Aspirin at baseline | 28 | 1.04 (0.80.-1.27) | 26 | 1.00 (0.76-1.24) | | | |
| No NSAID at baseline | 71 | 1.08 (0.93-1.23) | 67 | 0.77 (0.61-0.92) | 0.015 | 0.960 | 0.958 |
| NSAID at baseline | 12 | 1.08 (0.72-1.50) | 18 | 0.75 (0.45-1.05) | | | |
| No CVD drug, baseline | 47 | 0.97 (0.79.1.16) | 43 | 0.76 (0.57-0.96) | 0.001 | 0.234 | 0.213 |
| CVD drug at baseline | 36 | 1.22 (1.01-1.43) | 42 | 0.76 (0.57-0.96) | | | |
| No antihypertensives | 56 | 1.08 (0.91-1.25) | 51 | 0.74 (0.56-0.92) | 0.003 | 0.709 | 0.849 |
| Antihypertensive at baseline | 27 | 1.10 (0.85-1.34) | 34 | 0.80 (0.58-1.02) | | | |
| No TIA/stroke at baseline | 75 | 1.01 (0.85.1.15) | 75 | 0.77 (0.63-0.91) | <0.001 | 0.028 | 0.014 |
| TIA/stroke at baseline | 8 | 1.76 (1.31-2.21) | 10 | 0.74 (0.35-1.14) | | | |
| No stroke, TIA, MRI infarct at baseline | 68 | 0.99 (0.84-1.14) | 72 | 0.75 (0.61-0.90) | 0.001 | 0.025 | 0.098 |
| Stroke, TIA or MRI infart at baseline | 15 | 1.51 (1.18-1.83) | 13 | 0.84 (0.49-1.18) | | | |
| No CNS drugs at baseline | 63 | 1.03 (0.87-1.18) | 62 | 0.74 (0.58-0.90) | 0.002 | 0.17 | 0.274 |
| CNS drugs at baseline | 20 | 1.26 (0.98-1.54) | 23 | 0.82 (0.54-1.08) | | | |
| No diabetes | 73 | 1.05 (0.90-1.19) | 81 | 0.73 (0.59-0.87) | 0.508 | 0.014 | 0.334 |
| Diabetes anytime | 19 | 1.34 (0.94-1.73) | 4 | 1.40 (0.77-2.02) | | | |
| B vitamins, baseline | 17 | 0.86 (0.56.1.17) | 14 | 0.99 (0.65-1.32) | 0.246 | 0.962 | 0.034 |
| No B vitamins | 66 | 1.14 (0.99-1.29) | 71 | 0.72 (0.57-0.87) | | | |
| Initial brain < median | 43 | 1.16 (0.97-1.36) | 39 | 0.84 (0.63-1.04) | 0.002 | 0.157 | 0.844 |
| Initial brain > median | 40 | 0.99 (0.79-1.20) | 46 | 0.70 (0.52-0.89) | | | |
| Without APOE4 | 54 | 1.07 (0.89-1.24) | 63 | 0.74 (0.58-0.90) | 0.005 | 0.523 | 0.842 |
| With APOE4 | 29 | 1.11 (0.88-1.35) | 22 | 0.83 (0.56-1.10) | | | |
| MTHFR 677CC | 33 | 1.03 (0.81-1.08) | 35 | 0.82 (0.61-1.04) | 0.004 | 0.947 | 0.577 |
| MTHFR 677CT | 42 | 1.10 (0.90-1.05) | 41 | 0.72 (0.52-0.92) | | | |
| MTHFR 677TT | 8 | 1.23 (0.78-1.27) | 9 | 0.70 (0.27-1.12) | | | |
| TCN2 776CC | 21 | 1.08 (0.80-1.36) | 31 | 0.86 (0.63-1.08) | 0.001 | 0.733 | 0.263 |

TABLE 4-continued

Subgroup analyses: effects of several factors on the rate of atrophy and on the treatment effect

| | Placebo | | | Active treatment[a] | | | P value[b] | | |
|---|---|---|---|---|---|---|---|---|---|
| | | Atrophy rate | | | Atrophy rate | | | | |
| Factor | N | (95 % CI) %/y | | N | (95 % CI) % y | | Treatment | Factor | Interaction |
| TCNS 776CG | 14 | 1.02 | (0.83-1.21) | 45 | 0.75 | (0.56-0.94) | | | |
| TCN2 77GG | 18 | 1.23 | (0.93-1.53) | 9 | 0.51 | (0.08-0.93) | | | |
| Creatinine < median[c] | 39 | 1.01 | (0.81-1.21) | 42 | 0.63 | (0.43-0.82) | 0.002 | 0.036 | 0.489 |
| Creatinine < median | 44 | 1.15 | (0.96-1.34) | 42 | 0.91 | (0.71-1.10) | | | |
| tHcy < median | 44 | 0.89 | (0.70-1.08) | 40 | 0.79 | (0.59-0.98) | 0.001 | 0.068 | 0.019 |
| tHcy < median | 39 | 1.30 | (1.10-1.50) | 45 | 0.74 | (0.56-0.93) | | | |
| tHcy 1st quartile | 20 | 0.84 | (0.57-1.12) | 21 | 0.86 | (0.59-1.12) | 0.001 | 0.139 | 0.023 |
| 2nd quartile | 23 | 0.92 | (0.66-1.18) | 19 | 0.71 | (0.43-0.99) | | | |
| 3rd quartile | 18 | 1.05 | (0.76-1.34) | 24 | 0.78 | (0.53.1.03) | | | |
| 4th quartile | 21 | 1.52 | (1.25-1.79) | 21 | 0.71 | (0.44-0.98) | | | |
| Folate < median | 39 | 1.07 | (0.87-1.28) | 45 | 0.70 | (0.51-0.89) | 0.002 | 0.465 | 0.595 |
| Folate > median | 44 | 1.09 | (0.90-1.28) | 40 | 0.83 | (0.63-1.03) | | | |
| Vitamin $B_{12}$ < median | 37 | 1.07 | (0.86-1.28) | 47 | 0.77 | (0.58-0.96) | 0.002 | 0.976 | 0.832 |
| Vitamin $B_{12}$ > median | 46 | 1.09 | (0.91-1.28) | 38 | 0.75 | (0.55-0.96) | | | |
| HoloTC < median | 37 | 1.20 | (0.99-1.41) | 47 | 0.76 | (0.58-0.95) | 0.001 | 0.304 | 0.280 |
| HoloTC > median | 46 | 0.99 | (0.80-1.18) | 38 | 0.77 | (0.56-0.97) | | | |
| TC saturation < median | 35 | 1.22 | (1.01-1.44) | 45 | 0.76 | (0.57-0.97) | 0.001 | 0.261 | 0.188 |
| TC saturation > median | 48 | 0.98 | (0.79-1.16) | 40 | 0.77 | (0.57-0.97) | | | |

Abbreviations:
APOE, gene for apolipoprotein E;
CVD, cardiovascular disease;
HoloTC, holotranscobalamin;
MTHFR, gene for methylenetetrahydrofolate reductase;
NSAID, non-steroidal anti-inflammatory drug;
TCN2, gene for transcobalamin-2;
tHcy, plasma total homocysteine;
TIA, transient ischemic attack
[a]Active treatment group received daily supplements of folic acid (0.8 mg), vitamin $B_{12}$ (0.5 mg) and vitamin $B_6$ (20 mg) for 24 months.
[b]ANOVA was used to examine the effect of each factor on atrophy rate and its possible interaction with the treatment category; all analyses were adjusted for age at baseline.
[c]Ranked according to sex.

Outcome

Treatment with B vitamins for 24 months significantly slowed the rate of brain atrophy. After adjustment for age, the rate of brain atrophy/year was 29.6% less in the active group compared to the placebo group (0.76% [95% CI, 0.63-0.90] vs. 1.08% [0.94-1.22], P=0.001). Additional adjustment for the above-mentioned variables only marginally changed the decrease to 27.1% (rate of atrophy: 0.78% (0.64-0.91] vs. 1.07% [0.94-1.21], P=0.003). If the analysis was confined to the biologically compliant subjects (n=136), the effect of treatment was slightly greater with a reduction in atrophy rate of 31.1% (rate of atrophy: 0.73% [0.57-0.88] vs. 1.06% [0.90-1.22], P=0.004 after multi-adjusted analysis).

Figure 2:
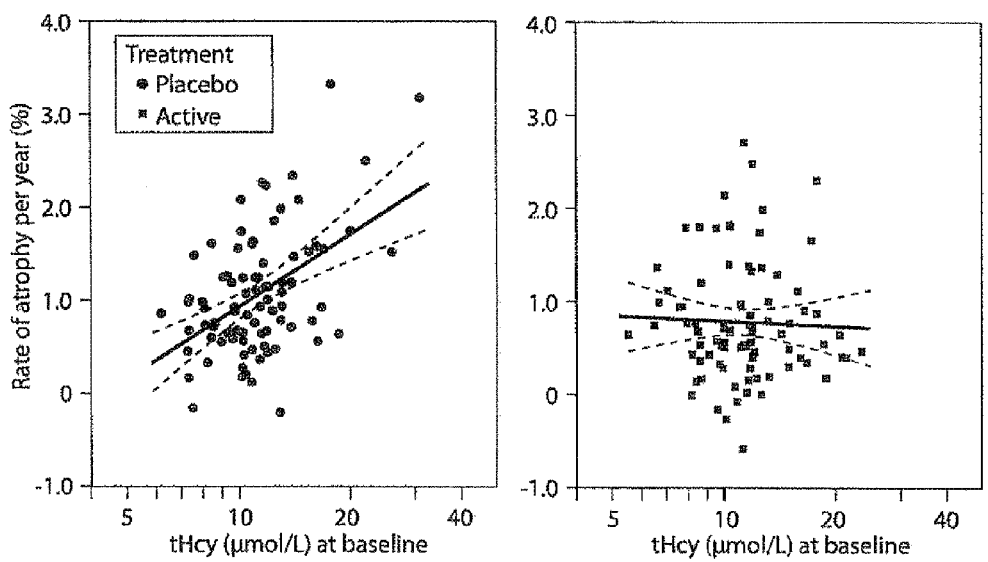
FIG. 2 shows atrophy rate by baseline tHcy. Linear regression lines with 95% mean prediction intervals. $R^2$ for placebo group (n=83) was 0.242 (P=0.001) and for the treatment group (n=85) was 0.001 (P=0.74).

In addition, a significant interaction was found between baseline tHcy and treatment (log tHcy x treatment, P=0.001). In the placebo group, tHcy at baseline showed a striking positive relationship to the rate of atrophy ($R^2$=0.24), whereas this association was absent in the active group (FIG. 2). Neither baseline folate nor the cobalamin markers showed such a relation.

Figure 3:
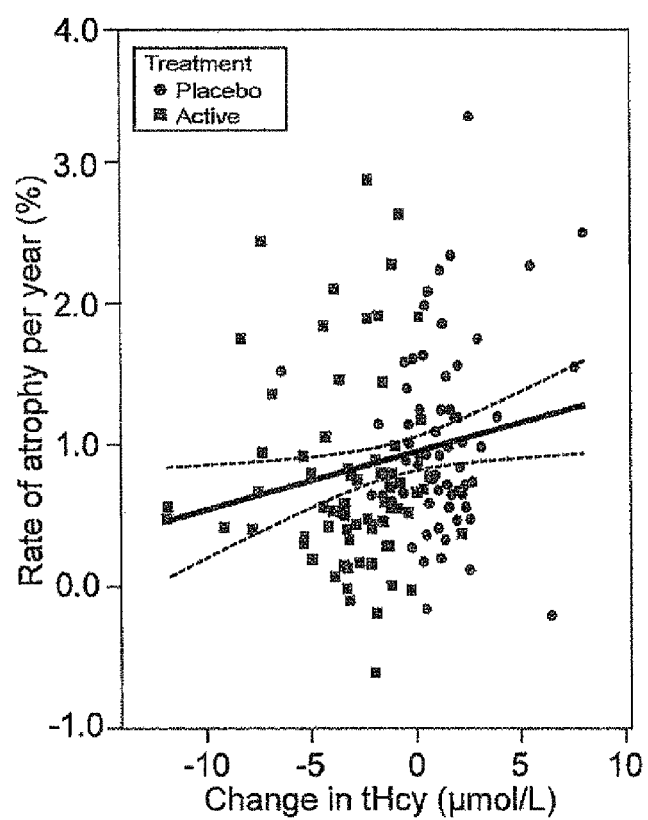
FIG. 3 shows atrophy rate by change in tHcy over a two year period. Subjects in this analysis were a subset (66/83) placebo; 70/85 active treatment) who showed biochemical evidence of good compliance. Linear regression with 95% mean prediction intervals, adjusted for age at baseline; standardised beta=0.22, P=0.011.
Figure 4:
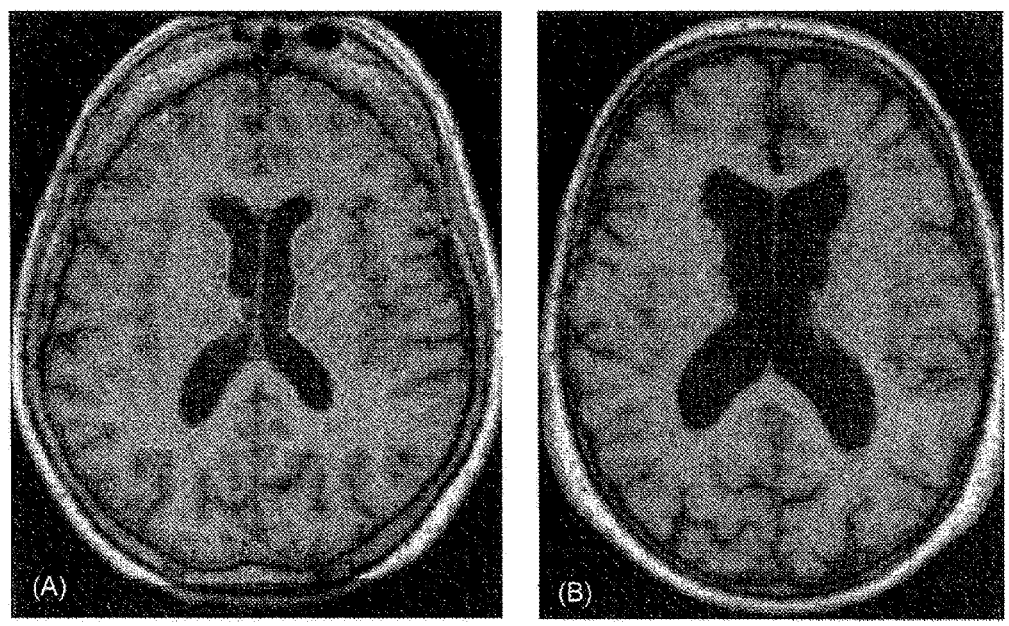
FIG. 4 shows selected subtraction MRI scans. (A) Subtraction image of female participant in placebo group, age 79 y at baseline, whose tHcy concentration increased by 8 µmol/L from a baseline value of 22 µmol/L over two y. Colours show expansion (red/yellow) or contraction (blue/light blue) of the brain of 0.3 to 1.0 mm, with the lightest colour indicating the biggest change. Atrophy rate 2.50% per y. Atrophy is most strongly appearing here as enlargement of the ventricles. (B) Subtraction image of female participant in active treatment group, age 72 y at baseline, whose tHcy concentration decreased by 12 µmol/L from a baseline value of 24 µmol/ over two y. Colours show expansion (red/yellow) or contraction (blue/light blue) of the brain of 0.3 to 1.0 mm, with the lightest colour indicating the biggest change. Atrophy rate 0.46% per y. There is no clear visible pattern of atrophy.

Atrophy was also examined in relation to the change in tHcy, folate and cobalamin markers from baseline to follow-up (Table 5). Rate of atrophy was significantly associated with the change in tHcy, and inversely with change in holoTC and TC saturation. Furthermore, when the analyses were confined to the biologically compliant subjects, the effects became stronger and change in folate and cobalamin also became significant. There was no association with change in cystathionine levels. Thus, the greater the improvement in folate or cobalamin status, the slower the rate of atrophy. Conversely, those subjects whose folate or cobalamin status declined were at increased risk of atrophy, illustrated in FIG. 3, using tHcy as a marker. FIG. 4 shows subtraction cranial MRI scans from a participant in the placebo group whose tHcy concentration increased, and from a member of the active treatment group whose tHcy concentration decreased, over the two-year period. Both subjects started with similar tHcy concentrations but the participant taking placebo showed a marked increase in tHcy over the two years, while the participant taking active treatment showed a marked fall in tHcy over this period. The rate of atrophy was more than 5-times slower in the participant taking B vitamins than in the subject taking placebo.

TABLE 5

Associations of rate of atrophy with changes in plasma biochemical markers upon treatment[a]

| Change in marker | As randomised | | Compliant subjects[c] | |
|---|---|---|---|---|
| | Partial r[d] (n-166) | P | Partial r[d] (n = 134) | P |
| tHcy | 0.19 | 0.017 | 0.25 | 0.004 |
| Folate | −0.13 | 0.096 | −0.29 | 0.001 |
| Vitamin $B_{12}$ | −0.05 | 0.516 | −0.27 | 0.002 |
| HoloTC | −0.20 | 0.011 | −0.25 | 0.004 |
| TC saturation | −0.22 | 0.004 | −0.25 | 0.005 |
| Cystathionine | 0.06 | 0.472 | 0.03 | 0.708 |

Abbreviations:
HoloTC, holotranscobalamin;
TC saturation, ratio of holoTC to total TC; tHcy, plasma total homocysteine
[a]Active treatment group received daily supplements of folic acid (0.8 mg), vitamin $B_{12}$ (0.5 mg) and vitamin $B_6$ (20 mg) for 24 months.
[b]All subjects;
[c]Subjects that were biologically compliant, defined by an increase from baseline to follow-up in plasma folate of >10 nmol/L and in cobalamin of >150 pmol/L to identify subjects in either group that had taken B-vitamin supplements correctly or independent or randomisation code.
[d]Adjusted for age, baseline diastolic blood pressure, baseline creatinine, initial brain volume and log baseline tHcy.

The effects in various subgroups are shown in Table 4. There were no significant interactions between treatment and the following variables: age, sex, category of MCI, normalised initial brain volume, hypertension, use of non-aspirin NSAIDs, smoking, creatinine, APOE4 and MTHFR 677C>1. In line with the interaction with baseline tHcy described above, in participants with baseline tHcy below the median the active treatment was associated with 11.2% slower rate of atrophy, whereas those with baseline tHcy above median showed a 43.0% reduction in atrophy ($P_{interaction}$=0.019). When further categorised tHcy into quartiles, there was no effect of treatment in those in the lowest quartile (tHcy≤9.5 μmol/L), whereas there was a 53.3% reduction in rate of atrophy in those in the $4^{th}$ quartile of tHcy (>13.0 μmol/L) treated with B vitamins vs. Placebo ($P_{treatment}$=0.001: $P_{tHcy}$=0.139; $P_{interaction}$=0.023). An interaction between treatment and a history of stroke or TIA at baseline was found: those in the placebo group with a previous event had an atrophy rate per year of 1.76% [1.31-2.21] compared with 1.01% [0.86-1.15] for those without an event. Those in the active treatment group had rates of 0.74% [0.35-1.14] and 0.77% [0.63.0.91] ($P_{treatment}$=0.001; $P_{stroke}$=0.028; $P_{interaction}$ 0.014), respectively. This interaction with stroke was no longer significant (P=0.098) when subjects with silent infarcts seen on MRI were included as well, although there was still a significant effect of stroke overall on atrophy rate (P=0.025). Regular use of aspirin showed a tendency to interact with treatment $P_{treatment}$=0.021; $P_{aspirin}$=0.19; $P_{interaction}$ 0.052); in those taking aspirin the treatment appeared less effective. A subset of participants reported taking multivitamin supplements containing B vitamins prior to the trial. (Table 1) and in these there was a significant interaction with treatment (P=0.034) such that active treatment was no longer effective. This lack of effect may be related to their low tHcy (geometric mean 9.8 [9.0-10.5] μmol/L) and high folate (37.5 [31.5-5-44.7] nmol/L) already at baseline.

Furthermore, although the study was not powered to detect an effect of treatment on cognition it was noted that some of the final cognitive test scores were correlated to the rate of atrophy. Multiple linear regression showed that the main factors that significantly determined the MMSE score at the end of the study were baseline MMSE score (partial re-0.42, P=<0.001), rate of brain atrophy (partial r=−0.36, P=<0.001) and age (partial r=0.20, P=0.01); the adjusted $R^2$ was 0.33. The same factors determined the final TICS-M score: baseline TICS-M (partial r=0.39, P<0.001), atrophy rate (partial r=−0.36, P<0.001), and age (partial r=0.27, P=<0.001); the adjusted $R^2$ was 0.39.

Safety Outcomes in the Whole Cohort

The overall B vitamin was very good in the whole cohort of 271 participants. Only 7 participants (2.5%) had plasma folate concentrations of <7 nmol/L and 6 (2.2%) had vitamin $B_{12}$ concentrations of <1 50 pmol/L at baseline. Since the vitamin analyses were done after the trial ended, these subjects, although classified as vitamin deficient, were not treated medically unless diagnosed by their GP.

Altogether 48 subjects were lost to follow-up the whole trial, 28 in the active group and 20 in the placebo group, Reasons for withdrawal are shown in Table 6 below. There were no significant safety issues and no significant differences in adverse events, except that there were fewer subjects in the active treatment group who showed a loss of vibration sense (Table 6). The time to drop out was shorter in the active group, even after excluding the immediate dropouts.

TABLE 6

Withdrawals and adverse events

| | Placebo (n = 133) | | Active treatment[a] (n = 133) | | |
|---|---|---|---|---|---|
| | Mean or n | SD or % | Mean or n | SD or % | P Value[b] |
| Total withdrawals[c] | 20 | 15.0 | 23 | 17.3 | |
| Time to withdrawal (d) | 441 | 179 | 298 | 197 | 0.017 |
| Self-withdrawal | 9 | 6.8 | 11 | 8.3 | |
| Time to withdrawal (d) | 469 | 115 | 231 | 144 | <0.001 |
| Cancer withdrawal | 8 | 6.0 | 5 | 3.8 | |
| Time to withdrawal (d) | 370 | 229 | 394 | 186 | |
| Exclusion criterion withdrawal | 1 | | 1 | | |
| Time to withdrawal (d) | 390 | | 433 | | |
| Other | 2 | | 4 | | |
| Time to withdrawal (d) | 620 | 145 | 231 | 231 | |
| Change in depression score (GDS) | 0.018 | 3.6 | −0.073 | 3.4 | |
| Loss of vibration sense | 13 | 9.8 | 3 | 2.2 | 0.019 |
| Myocardial infarction | 1 | | 1 | | |
| Stroke | 1 | | 3[d] | | |

TABLE 6-continued

Withdrawals and adverse events

|  | Placebo (n = 133) Mean or n | SD or % | Active treatment[a] (n = 133) Mean or n | SD or % | P Value[b] |
|---|---|---|---|---|---|
| Death | 0 |  | 2[e] |  |  |
| Time to death (d) |  |  | 490 |  |  |
| Total adverse events | 271 |  | 242 |  |  |

Abbreviation:
GDS, Geriatric Depression Scale
[a]Active treatment group received daily supplements of folic acid (0.8 mg), vitamin $B_{12}$ (0.5 mg) and vitamin $B_6$ (20 mg) for 24 months.
[b]Only P values <0.1 are shown.
[c]Excluding 5 who withdrew before starting the tablets and 2 who withdrew after the 24 month visit.
[d]Includes one of the 2 participants who died.
[e]One hemorrhagic stroke; one pulmonary embolism Discussion B vitamin treatment led to a difference in final tHcy concentration of 31.7% compared with the placebo, and was accompanied by a reduction in the rate of brain atrophy of almost 30%. No safety issues were found, so it can be concluded that high doses of B vitamins can be used to reduce the rate of atrophy of the brain in elderly people with MCI.

The treatment effect was greatest in those with the highest baseline level of tHcy, with a reduction in atrophy rate of 53% in those in the top quartile of tHcy (>13.0 μmol/L). There was no effect of treatment on atrophy in those in the bottom quartile (≤9.5 μmol/L). In the placebo group, the rate of atrophy was related to the baseline concentration of tHcy. In contrast, in the group on active treatment there was no relationship at all between baseline tHcy and the rate of atrophy; this finding may indicate that raised tHcy is a direct cause of the atrophy and/or that tHcy is a marker for low-normal levels of the vitamins which are the causal factors.

In the present study, it was found that an increase in either vitamin $B_{12}$ status or in folate status was associated with a reduced rate of atrophy.

Conclusions

This study was carried out in the UK, where voluntary fortification of foods with folic acid is permitted but where there is no mandatory fortification. The effect of treatment was dependent on baseline tHcy, with those in the upper three quartiles, i.e. 9.5 μmol/L, showing a significant slowing of atrophy upon treatment compared with those in the lowest quartile. In the USA, which has a mandatory fortification, 13.6% of those ≥60 years old had tHcy concentration >13 μmol/L in 2003-4 (Pfeiffer et al., 2008), a level at which we found a >50% reduction in the rate of atrophy upon treatment with high doses of B vitamins. The median tHcy concentration in those ≥60 years old in the USA is 10.1 μmol/L, suggesting that a substantial proportion of those with MCI could benefit from the intervention.

It is considered that the findings are relevant to cognitive decline in people with MCI. First, in studies over longer periods (up to 5 years) it has been found that the rate of whole brain atrophy in MCI is correlated with cognitive decline in several tests, including the MMSE (Jack et al., 2004). Second, when we looked for significant predictors of the final cognitive test score, the rate of atrophy was one of the three main factors determining the final MMSE and TICS-M scores. Third, two other randomised controlled trials of homocysteine-lowering treatments have shown effects on cognition: a trial in which normal participants with baseline tHcy levels >13 μmol/L were treated with folic acid (0.8 mg/d) for three years showed a beneficial effect on several cognitive tests (Durga et al., 2007). Since the rate of brain atrophy is more rapid in subjects with MCI who convert to Alzheimer's disease, high doses of folic acid, $B_6$ and $B_{12}$ may be considered to slow the conversion from MCI to Alzheimer's disease.

EXAMPLE 2

Additional analysis was carried out to determine whether (a) treatment with B vitamins show effects on cognitive performance, b) whether baseline plasma tHcy level modified treatment effects on the rate of cognitive decline, c) which cognitive domains were most strongly associated with B vitamin treatment and d) were there any relevant clinical outcomes at the study end.

Methods

Study Protocol

The study protocol has been previously described in Example 1. Respondents to recruitment advertising (n=646) were screened by telephone for entry criteria and for MCI using a screening questionnaire, the Telephone Interview for Cognitive Status-modified (TICS-M) 15 (≥17 and ≤29) and a category fluency test (Morris, 1988). Those with MCI who were 70 years and older, had a study partner and had no exclusion criteria (dementia, active cancer, major stroke within past 3 months, treatment with methotrexate, anti-cancer or anti-epileptic drugs, or taking folic acid >300 μg/d], pyridoxine >3 mg/d or cobalamin >1.5 g/d] by mouth or any dose by injection; symptoms of severe depression assessed with the Geriatric Depression Scale (Yesavage J A, Psychopharmacol Bull 1988, 24:709-11) were invited into the study.

At first clinic visit the intention to treat (ITT) group included 266 subjects who gave written consent and were randomized to treatment or placebo. Other measures to confirm the MCI diagnosis [Petersen, 2007] with corroboration from a study partner were collected including the MMSE (>24/30), clinical dementia rating scale (CDR, =0.5), informant interview on cognitive decline in the elderly (IQCODE), questions on subjective memory complaints from the Cambridge examination for mental disorders of the elderly (CAMDEX)[20] and activities of daily living from the Cambridge Behavioural Inventory. The subjects were coded as amnestic or non-amnestic, -single or -multiple domain MCI according to cognitive test cut-off scores from the neuropsychological test battery described below. Non-amnestic MCI cases were included as the mechanism of action of B vitamins and homocysteine could relate to memory and non-memory domain functions.

Participants had a brief medical examination, provided blood and urine samples and were asked for consent to two cranial MRI scans, one at the start and one two years later at the end of treatment, if there were no contra-indications. The study was approved by a NHS research ethics committee (COREC 04/Q1604/100).

A full neuropsychological test battery was conducted by trained research nurses and psychologists blinded to the outcomes of the CDR and informant information. The battery included tests of episodic memory (HVLT-R (Brandt, 1991), CANTAB PAL and spatial recognition tasks [www.camcog.com]), semantic memory (Graded Naming Test [McKenna, 1989] and category fluency (CERAD, Morris, 1988) for supermarket items), executive function (Trailmaking A&B [Reitan], SDMT [Smith], CLOX (Royall, 1998)) and a test of selective attention (Map Search) [Robertson, 1994].

Participants were contacted by telephone at 3, 6, 12, 15 and 18 months after starting treatment to check compliance, adverse events and to administer the HVLT-R using the 6 different versions consecutively through the trial to avoid practice effects. After 24 months, participants returned to the clinic to repeat all tests including the cognitive test battery as at visit 1.

Treatment was started on the same day as the first structural MRI scan or on the day of the first clinic visit after randomisation, for those not having an MRI. Centralised telephone randomization was used with full allocation concealment and minimization for age, gender, TICS-M score, MRI consent). The treatment group received TrioBe Plus® (Meda AB/Recip AB, Box 906, Pipers väg 2A, SE-170 09 Solna, Sweden), containing 0.8 mg folic acid; 0.5 mg cyanocobalamin; 20 mg pyridoxine HCl. The placebo group received vitamin-free tablets. At the second visit or second MRI scan, participants returned the tablet bottles.

Blood Sampling and Assays (as Previously Described)

At baseline and after 24 months, blood samples were sent to a routine clinical laboratory for immediate haematological and biochemical variable determination. Samples containing EDTA were processed and stored. Plasma tHcy was determined by fluorescence polarization immunoassay with the Abbott IMx® analyzer. Plasma folate and cobalamin concentrations were determined with microbiological assays. Genomic DNA was extracted from blood using the Wizard DNA Purification Kit (Promega, Southampton, UK). ApoE genotypes (NCBI Entrez Gene: 348) were determined using a one-stage PCR method.

Statistical Analyses

Power calculations for this trial, based on rate of brain atrophy over two years, are described in Example 1. However a larger sample (n=223) of the ITT participants completed the secondary outcome measures (neuropsychological tests) for the analyses in this paper. Since the data is longitudinal a generalized linear mixed effects model was fitted using the binomial distribution with logit link for the HVLT-delayed recall (HVLT-DR) and MMSE and the Poisson distribution with log link for Category fluency. The parametric AFT survival model was fitted using the Weibull distribution for Trailmaking A. The choice of the binomial distribution for the HVLT-DR and MMSE is appropriate since the scores represent the number of correct answers from a set of predefined questions. The Poisson distribution was chosen for Category fluency since the score is the number of correct items in a timed interval. For reasons partly related to the interpretation of the CLOX test, this latter was analysed cross-sectionally by modelling CLOX1 at follow-up conditional to CLOX1 at baseline and CLOX2 at follow-up. The Gaussian distribution was used for the MMSE which is equivalent to using a linear mixed effects model. Since the CDR score is an ordered categorical outcome, it was analysed using the longitudinal cumulative logit model. However, as there were very few subjects with CDR score equal or greater than 1, the CDR score was recoded as a binary outcome 0 or {0.5 or over} and then a generalized linear mixed effects model was fitted using the Bernoulli distribution with logit link. Finally, generalized estimating equations were fitted to all outcomes to obtain comparative results to confirm conclusions derived from random effects models.

The models were initially performed without interaction terms to determine direct effects of treatment on cognition controlling for covariates including age, ApoE, gender and education. Thereafter, baseline tHcy was included in the interaction term, first as a continuous variable, and then as a binary variable. For ease of interpretation, results of this analysis are reported for tHcy as a binary variable rather than a continuous one. More specifically, study participants were classified as 'lower tHcy group' if their baseline tHcy level was below the median (11.3 micromol/L) or 'higher tHcy group' for the remainder.

The statistical analyses to one test per cognitive domain (HVLT for episodic memory, Category fluency for semantic memory, CLOX for attention & executive function and MMSE for global cognition) as each test required a different statistical model.

For all outcomes of interest, the analysis was started with a saturated model including all effects (main effects, two-way interaction effects and three-way interaction effects). The model was then reduced hierarchically using the likelihood-ratio test and the AIC (Aikake information criterion).

Results

Demographics

Of the 288 ITT sample randomised at first visit, 223 participants completed the second visit 2 years later and had the full repeated neuropsychological assessment. Reasons for withdrawal have been previously described in Example 1. The statistical analysis has been performed for the intention to treat recruits (placebo, n=134, treatment n=132).

The demographics for the treatment and placebo groups are presented in Table 7.

TABLE 7

Comparison of demographic variables for the treatment and placebo participants (ITT) using t-tests for continuous variables and $Chi^2$ for categorical variables.

| Variable | ITT Vitamin group (n = 132) Mean, SD | ITT Placebo group (n = 134) Mean, SD | P-value |
|---|---|---|---|
| Age at baseline (y) | 76.8, 4.9 | 76.8, 5.0 | 0.93 |
| Gender (M:F) | 47:84 | 49:85 | $Chi^2 = 0.9$ |
| Total education (y) | 14, 3.5 | 15, 3.2 | 0.47 |
| ApoE є4 carrier | 37% | 28% | $Chi^2 = 0.15$ |
| Smoker (ever) | 44% | 52% | $Chi^2 = 0.19$ |
| GDS (0-30)* | 5.98, 4.4 | 7.43, 4.9 | 0.01* |
| Systolic BP mmHg | 147, 22 | 147, 20 | 0.87 |
| Diastolic BP mmHg | 81, 11 | 80, 11 | 0.76 |
| BMI | 25.8, 3.8 | 26.3, 4.2 | 0.34 |
| Bodyweight kg | 70.6, 14.0 | 72.6, 13.6 | 0.25 |
| Height cm | 1.65, 0.1 | 1.66, 0.1 | 0.36 |
| Folate | 27.6, 18.0 | 27.3, 18.8 | 0.90 |
| B12 pmol/L | 363.1, 166.2 | 335.7, 105.2 | 0.11 |
| tHcy μmol/L | 11.8, 3.4 | 12.1, 4.0 | 0.50 |
| TC | 940.6, 190.0 | 937.7, 260.9 | 0.92 |
| TC saturation | 8.0, 4.5 | 8.1, 3.6 | 0.98 |
| Holo-TC | 76.7, 50.7 | 74.9, 44.1 | 0.76 |
| Creatinine μmol/L | 95.9, 16.8 | 98.1, 16.4 | 0.28 |

TABLE 7-continued

Comparison of demographic variables for the treatment and placebo participants (ITT) using t-tests for continuous variables and Chi$^2$ for categorical variables.

| Variable | ITT Vitamin group (n = 132) Mean, SD | ITT Placebo group (n = 134) Mean, SD | P-value |
|---|---|---|---|
| Treatment period | 2.1, 0.08 | 2.1, 09 | 0.64 |
| Glutamate | 29.5, 10.8 | 30.1, 11.1 | 0.66 |
| Taurine | 43.7, 9.5 | 42.9, 11.3 | 0.57 |

*GDS: 0-10 = mild, 11-20 = moderate, 21-30 = severe depressive symptoms.

There were no differences between the groups on any of the baseline measures. The demographics of the completers were similar. Mean cognitive scores including MMSE 28.13 (1.76), TICS-M 24.85 (2.8), and HVLT total recall, 23.2 (5.2) were all higher than the cut-off points for MCI. The mean GDS score was 6.7 (4.8) indicating only mild depressive symptoms. Baseline folate, vitamin $B_{12}$ and tHcy were all in the normal range for age. Cognitive scores below the MCI cut-offs were used for amnestic or non-amnestic, -single or -multiple domain MCI classification at visit 1. 21 subjects had no scores below the cut-offs, but 10 of these had a CDR rating of 0.5. Thus, only 11 (4%) of those randomised into the study by the telephone screening method used, appeared to have no objective cognitive impairment at randomisation in spite of being classified as MCI at recruitment. They were not excluded from the study.

Effect of B Vitamin Treatment on Longitudinal Cognition

The effect over time of B vitamin treatment on HVLT delayed recall (HVLT-DR), MMSE, CLOX and Category fluency scores was investigated.

There was a statistically significant improvement in CLOX1 scores at follow-up in the vitamin treated group. The odds of correctly answering an item from CLOX1 at follow-up, for subjects starting with similar CLOX1 at baseline, is 30% higher in treated subjects (P=0.014) relative to placebo. The model controls for CLOX2 at follow-up in addition to CLOX1 at baseline, as well as for confounders age, education, ApoE and gender. There was no significant interaction between treatment and baseline tHcy level.

The effect of treatment on the other cognitive tests was significant when tHcy at baseline was included as an interaction term. The final model shows that those in the 'higher Hcy group' on placebo showed significant cognitive decline while treated subjects in the 'higher tHcy group' showed no decline. On average cognitive scores in the 'lower tHcy group' did not decline over time for both treated and placebo groups. The significant difference shown by the model was between treatment and placebo in the 'higher tHcy group' only.

FIG. 5a gives the estimated odds ratio over time of correctly answering a question from the HVLT-DR for someone in the 'higher tHcy group' who has been treated compared to that same person if not treated. The odds ratio significantly increase over time. For example, the odds of a correct answer 2 years after starting the treatment for someone in the 'higher tHcy group' is 74% greater than his odds if no treatment was taken (P-value=0.004). FIG. 5b shows how the estimated total HVLT-DR score changes over time in the 'higher tHcy group' for the average subject according to treatment status. Treatment resulted in maintenance of performance while the placebo group scores declined over time. For the HVLT-DR score, we removed data from the 0 month time-point to eliminate the initial practice effects.

FIG. 6a shows that the odds of a correct answer on the MMSE 2 years after starting the treatment for someone in the 'higher tHcy group' are 44% greater than if no treatment was taken (P-value=0.003). FIG. 6b shows how the estimated total MMSE score changes over time in the 'higher tHcy group'. Those on placebo showed a decline in MMSE while those on treatment showed no significant change.

FIG. 7 gives the average Category fluency score over time for someone in the 'higher tHcy group' who has been treated compared to that same person if not treated. For example, the average number of words 2 years after starting the treatment for someone in the 'higher tHcy group' is 12% greater than his average number if no treatment was taken (P-value=0.003).

Figure 8:
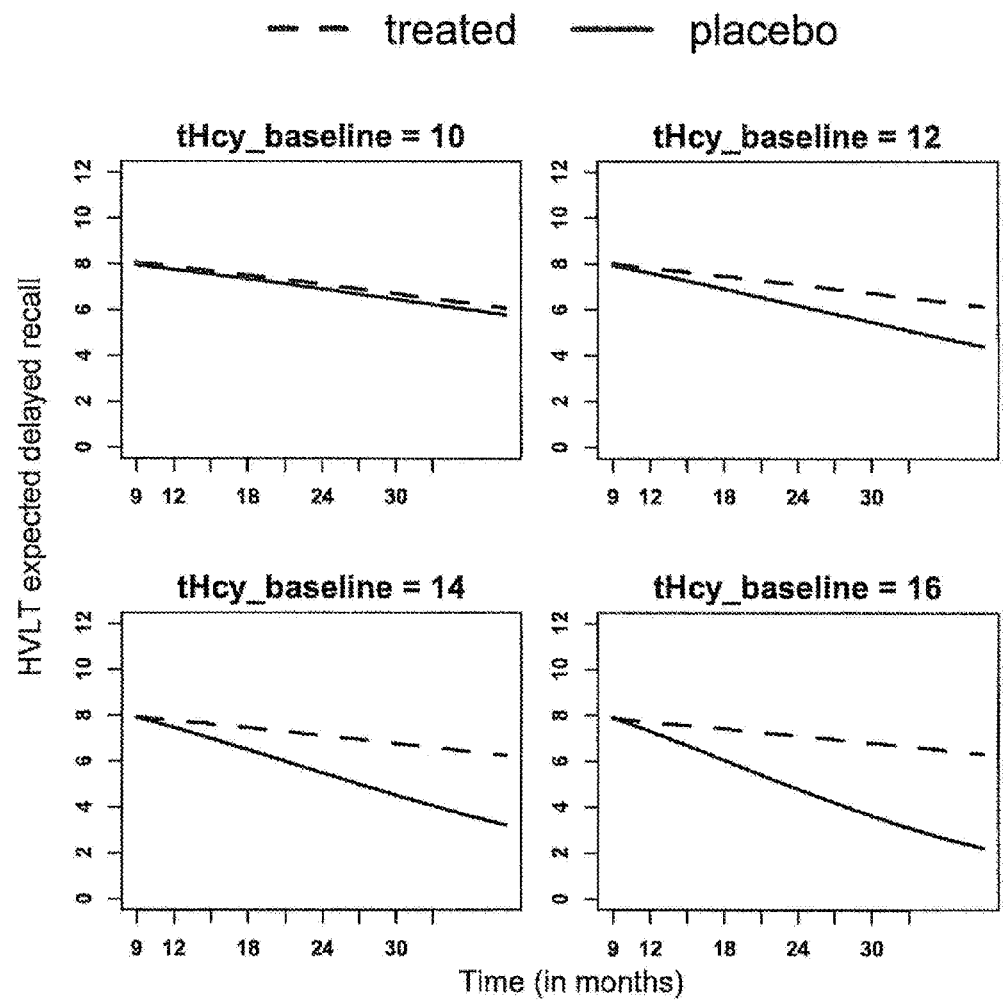
FIG. 8 shows HVLT-DR scores over time in treated and placebo groups according to the baseline tHcy concentrations.

FIG. 8 gives the change in HVLT-DR scores over time according to four different baseline concentrations of tHcy. The effect of treatment in slowing the decline in the score is limited to subjects with baseline tHcy above 10 µmol/L, the treatment effect being greater the higher the baseline tHcy level.

Effect of B Vitamin Treatment on Longitudinal Clinical Outcome

Figure 9:
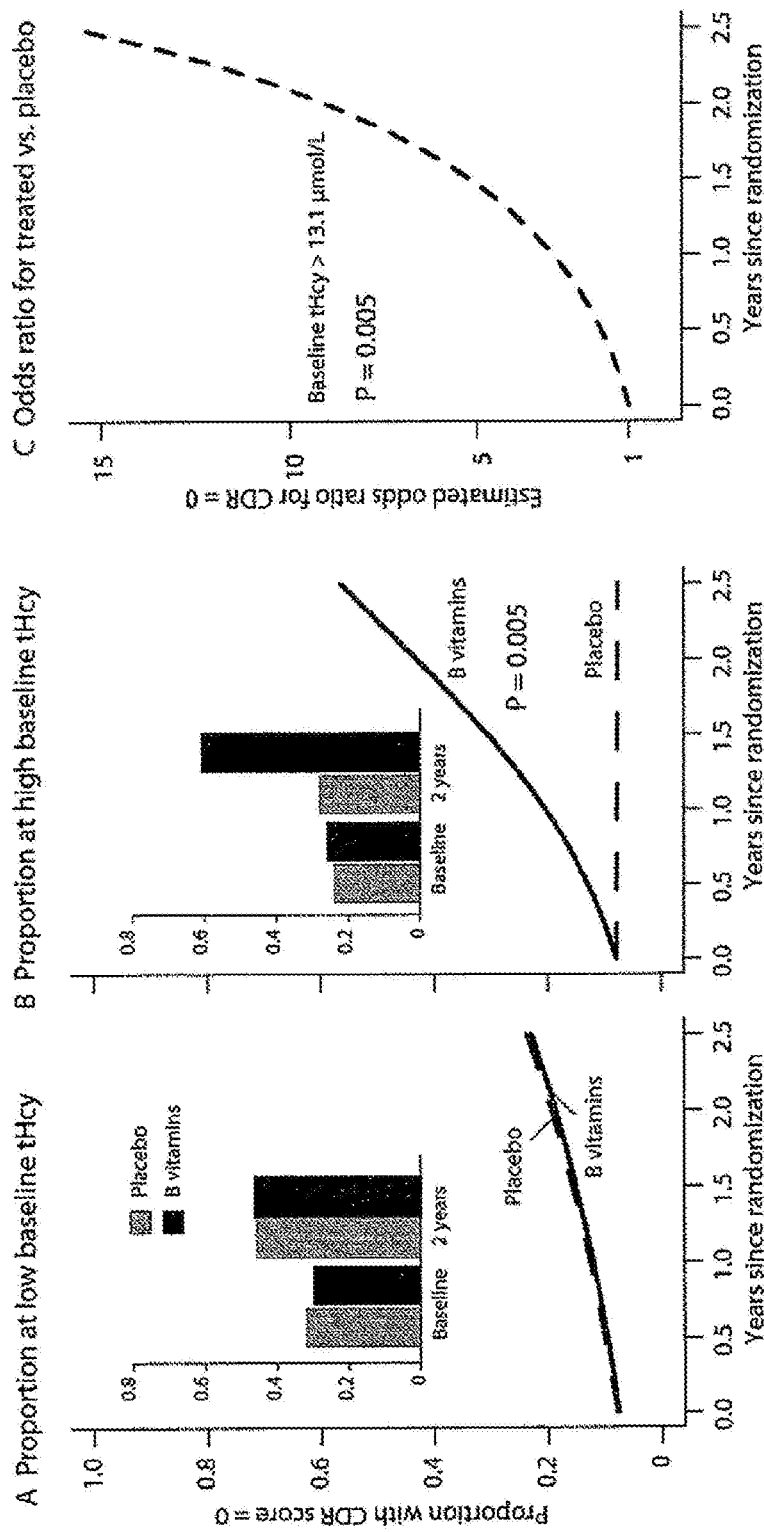
FIG. 9 is a graph showing the effect of treatment on the proportion of subjects with a CDR score of zero according to whether the baseline tHcy concentrations were below and above the $75^{th}$ percentile.
Figures 10A, 10B, 10C:
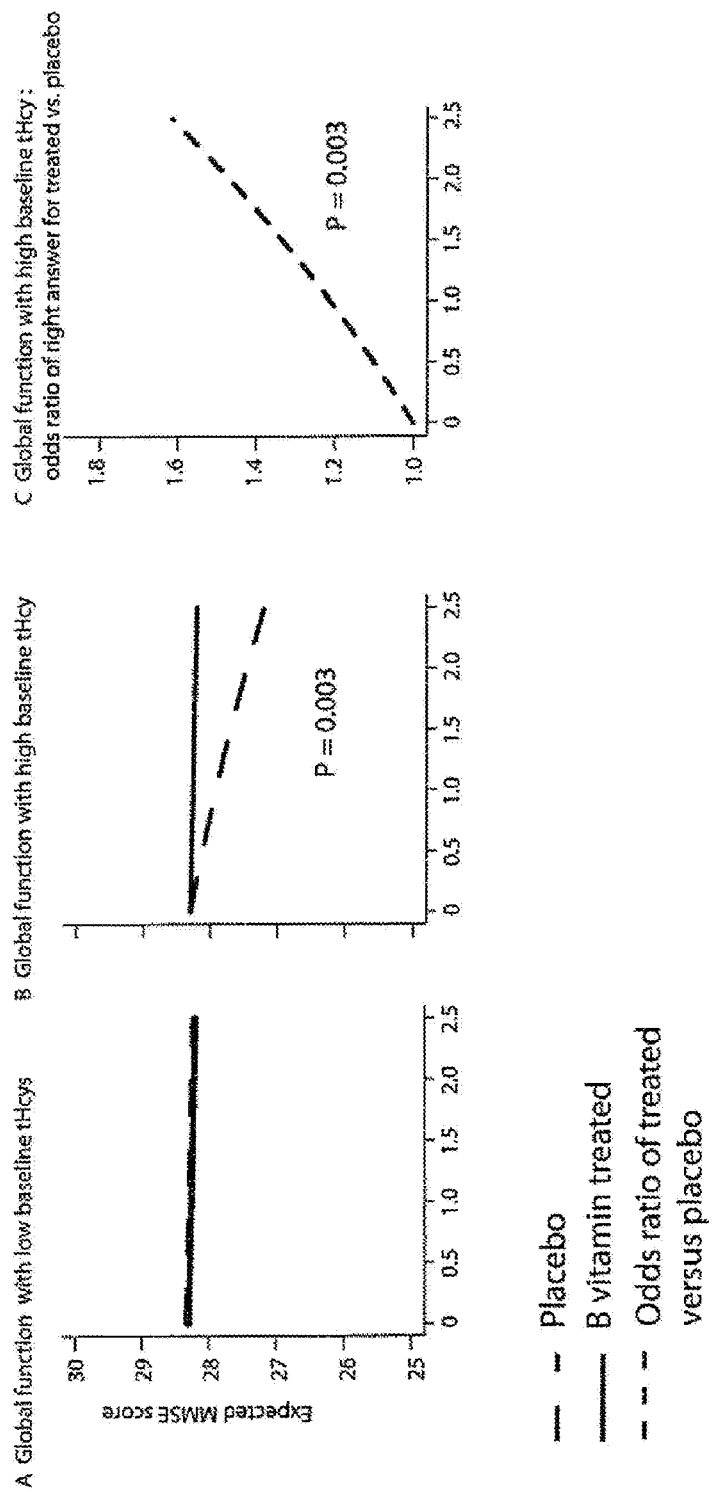
FIG. 10(a) shows how the estimated total MMSE score changes over time in the 'low tHcy group'
FIG. 10(b) shows the respective MMSE changes in the high tHcy group. Only subjects in the 'high tHcy group' benefitted from B vitamin treatment. Those on placebo showed a decline in MMSE while those on B vitamins showed no significant change.
FIG. 10(c) shows the odds over time of a correct answer on an item on the MMSE for someone in the 'high tHcy group' who has received B vitamins compared to the same person if treated with placebo. The odds of a correct answer to a question in the MMSE 2 years after starting the treatment for someone in the 'high tHcy group' was 44% greater than if no treatment was taken (odds ratio=1.44, P=0.003).
Figures 10D, 10E, 10F:
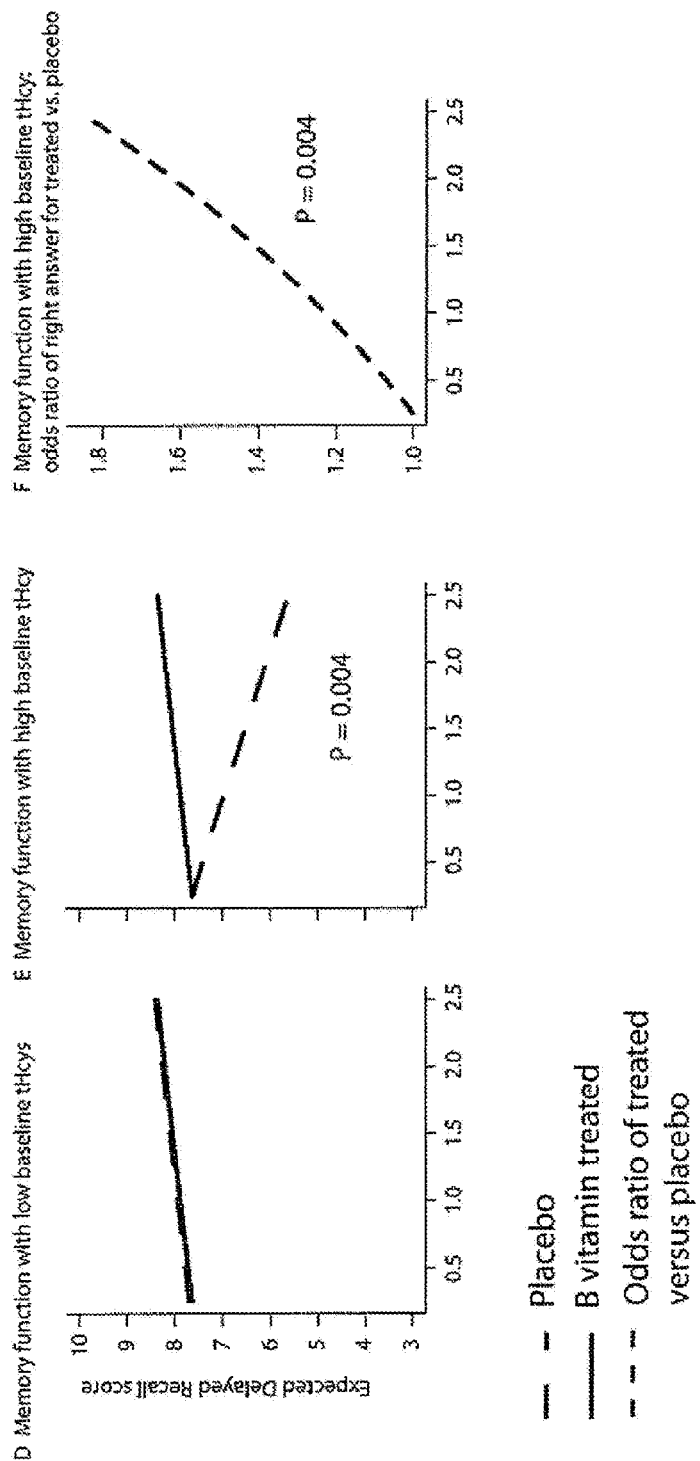
FIG. 10(d)-(f) show a similar set of results for HVLT-DR. Also here, for someone with elevated tHcy the B vitamin treatment resulted in maintained performance, while for that person taking the placebo the score declined over time. For the HVLT-DR model, data from the 0-3 month time period was excluded to reduce the initial practice effects.
Figures 10G, 10H:
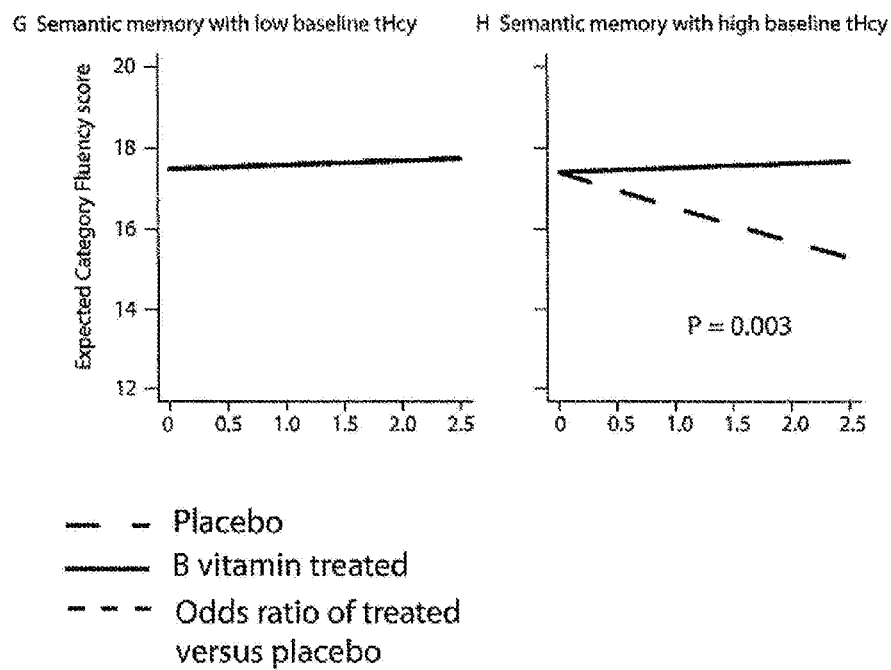
FIG. 10(g) and (h) shows the estimated average Category fluency score over time in the 'low' vs. 'high' tHcy groups, respectively. The average number of words 2 years after starting the B vitamin treatment for someone in the 'high tHcy group' is 12% greater than that person's average if no treatment was taken (P=0.003).

There was a significant effect of treatment on overall CDR scores when the population was stratified by tHcy quartiles. The sample composition at baseline in terms of CDR scores was almost the same for placebo [CDR=0: 29.8%, CDR –0.5: 70.2%, CDR=1: 0%] and treatment [28.9%, 70%, 1.1%] groups respectively. At outcome the corresponding composition in the placebo group was 41.4%, 55.3%, 3.3% and 50%, 47.8%, 1.2%, respectively in the treatment group. In participants whose baseline tHcy was in the upper quartile (>13.12 µmol/L), the odds of having a CDR=0 two years after starting the treatment is 9 times greater than if no treatment was taken (odds ratio at year 2=9, P=0.004). FIG. 9 shows the effect of treatment on the proportion with a CDR score of zero, from which it can be seen that the treatment effect was limited to those in the upper quartile for tHcy.

Discussion

The results show an effect of B vitamin treatment in slowing decline in cognitive test performance over time. In an executive function test, the CLOX, the effect of treatment on improved scores was direct, while for other cognitive domains the effect was dependent on baseline tHcy level. There was no cognitive decline in the treatment group compared with an increased rate of decline in the placebo group in those with plasma tHcy levels above 11.3 µmol/L. This effect was shown for global cognition, episodic memory, and semantic memory. The effects were most striking for episodic memory, where treatment for two years in a subject with a high level of tHcy gave a 74% higher likelihood of correct word recall compared with placebo, and there was a significant difference in the rate of decline between the treatment and placebo groups. Those with higher tHcy levels at baseline were more likely to respond to treatment with B vitamins, having lower tHcy levels at the end of the trial and there was a reduced rate of brain atrophy in the treated group, independent of tHcy level. For those with low tHcy at baseline there was no effect of treatment on cognition, but cognition remained as stable as for those with high tHcy who were on treatment.

The results also show an effect on a widely used clinical assessment tool, the CDR. In subjects in the upper quartile of tHcy, there was a striking increase in the proportion of subjects with a CDR of zero in those who were treated, but not in the placebo group. The clinical improvement shown by the CDR provides some evidence for a reversal of cognitive impairment in those with MCI whose tHcy has been lowered by B vitamin treatment.

REFERENCES

Aisen P S, Neurology 2008; 70: 2020-2021.
Aisen P S, Schneider L S, Sano M, Diaz-Arrastia R, van Dyck C H, Weiner M F, et al., Jama 2008; 300: 1774-83.
Anstey K J, Jorm A F, Reglade-Meslin C, Mailer J, Kumar R, von Sanden C, et al. Psychosom Med 2006; 68: 778-85.
Antoniades C, Shirodaria C, Leeson P, Baarholm O A, Van-Assche T, Cunnington C, et al. Circulation 2009; 119: 2507-2515.
Bleie O, Refsum H, Ueland P M, Vollset S E, Guttormsen A B, Nexo E, et al.; Am J Clin Nutr 2004; 80: 641-8.
Bradley K M, Bydder G M, Budge M M, Hajnal J V, White S J, Ripley B D, et al. Br J Radiol 2002; 75: 506-13.
Brandt J, Welsh K A, Breitner J C S, Folstein M F, Helms M, Christian J C. Arch. Neurol. 1993; 50: 599-603.
Brandt J. The Hopkins Verbal Learning Test: Development of a new memory test with six equivalent forms. Clinical Neuropsychologist 1991; 5:125-42.
Budge M, Johnston C, Hogervorst E. et al. Plasma total homocysteine and cognitive performance in a volunteer elderly population. Ann N Y Acad Sci 2000; 903:407-10.
Carlson N E, Moore M M, Dame A, Howieson D, Silbert L C, Quinn J F, et al. Neurology 2008; 70: 828-33.
Clarke R, Smith A D, Jobst K A, Refsum H, Sutton L, Ueland P M.; Arch Neurol 1998; 55: 1449-55.
Clarke R. Homocysteine-lowering vitamin B supplements do not improve cognitive performance in healthy older adults after two years. Evid Based Ment Health 2007; 10:27.
Clarke R J, Bennett D A. B vitamins for prevention of cognitive decline: insufficient evidence to justify treatment. JAMA 2008; 300:1819-21.
DeCarli C; Lancet Neurol 2003; 2: 15-21.
De Jager C A, Budge M M, Clarke R.; Int J Geriatr Psychiatry 2003; 18: 316-24.
Den Heijer T, Vermeer S E, Clarke R, Oudkerk M, Koudstaal P J, Hofman A, et al.; Diabetolgia 2003b.
Durja J, van Boxtel M P, Schouten E G, Kok F J, Jolles J, Katan M B, et al.; Lancet 2007: 208-16.
Ellas M F, Robbins M A, Budge M M, et al. Homocysteine, folate, and vitamins B6 and B12 blood levels in relation to cognitive performance: the Maine-Syracuse study. Psychosom Med 2006; 68:547-54.
Enzinger C, Fazekas F, Matthews P M, Ropele S, Schmidt H, Smith S, et al. Neurology 2005; 64: 1704-11.
Erickson K I, Suever B L, Prakash R S, Colcombe S J, McAuley E, Kramer A F.; Brain Res 2008; 1199: 20-26.
Eussen S J, de Groot L C, Joosten L W, et al. Effect of oral vitamin B-12 with or without folic acid on cognitive function in older people with mild vitamin B-12 deficiency: a randomized, placebo-controlled trial. Am J Clin Nutr 2006; 84:361-70.
Folstein M F, Folstein S E, McHugh P R. Mini-mental state; J Psychiatr. Res. 1975; 12: 189-198.
Fox N C, Scahill R I, Crum W R, Rossor M N. Neurology 1999; 52:1687-1689.
Homocysteine Lowering Trialist Collaboration; Am J Clin Nutr 2005; 82: 806-12.
Jack C R, Jr., Shiung M M, Gunter J L, O'Brien P C, Weigand S D, Knopman D S, et al. Neurology 2004; 62:591-600.
Jack C R, Jr., Shiung M M, G Weigand S D, O'Brien P C, Gunter J L, O'Brien P C, Boeve B F, et al. Neurology 2005; 65: 1227-31.
Jorm A F, Jacomb P A. The Informant Questionnaire on Cognitive Decline in the Elderly (IQCODE): socio-demographic correlates, reliability, validity and some norms. Psychol Med 1989; 19:1015-22.
Killiany R J, Gomez-Isla T, Moss M, Kikinis R, Sandor T, Jolesz F, et al. Ann Neurol 2000; 47: 430-9.
McCaddon A, Davies G, Hudson P, Tandy S, Cattell H. Int J Geriatr Psychiatry 1998; 13: 235-239.
Molloy A M, Scott J M. Microbiological assay for serum, plasma, and red ceil folate using cryopreserved, microtiter plate method. Methods Enzymol 1997; 281:43-53.
Morris J C, Heyman A, Mohs R C, Hughes J P, Vanbelle G, Fillenbaum G, et al. Neurology 1989; 39: 1159-1165.
Morris J C. The Clinical Dementia Rating (CDR): current version and scoring rules. Neurology 1993; 43:2412-4.
Nurk E, Refsum H, Tell G S, et al. Plasma total homocysteine and memory in the elderly: the Hordaland Homocysteine Study. Ann Neurol 2005; 58:847-57.
Petersen R C, Roberts R O, Knopman D S, Boeve B F, Geda Y E, Ivnik R J, et al.; Neurol 2009; 66: 1447-55.
Petersen R C, Smith G E, Waring S C, Ivnik R J, Tangalos E G, Kokmen E.; Arch Neurol 1999; 56: 303-308.
Pfeiffer C M, Osterloh J D, Kennedy-Stephenson J, Picciano M F, Yetley E A, Rader J I, et al. Trends in circulating concentrations of total homocysteine among US adolescents and adults: findings from the 1991-1994 and 1999-2004 National Health and Nutrition Examination Surveys. Clin Chem 2008; 54: 801-813.
Plassman B L, Langa K M, Fishter G G, Heeringa S G, Weir D R, Ofstedal M B, et al. Ann Intern Med 2008; 148: 427-34.
Refsum H, Nurk E, Smith A D, Ueland P M, Gjesdal C G, Bjelland I, et al.; J Nutr 2006; 136: 1731S-40S.
Refsum H, Smith A D. Homocysteine, B vitamins, and cardiovascular disease. N Engl J Med 2006; 355:207; author reply 9-11.
Refsum H, Johnston C, Guttormsen A B, Nexo E. Holotranscobalamin and total transcobalamin in human plasma: determination, determinants, and reference values in healthy adults. Clin Chem 2006; 52:129-37.
Resnick S M, Pham D L, Kraut M A, Zonderman A B, Davatzikos C; J Neurosci 2003; 23: 3295-301.
Ries M L, Carlsson C M, Rowley H A, Sager M A, Gleason C E, Asthana S, et al.; J Am Geriatr Soc 2008; 56: 920-34.
Risacher S L, Saykin A J, West J D, Shen L, Firpi H A, McDonald B C; Curr Alzheimer Res 2009; 6: 347-61.
Robbins T W, James M, Owen A M, Sahakian B J, McInnes L, Rabbitt P. Cambridge Neuropsychological Test Automated Battery (CANTAB): a factor analytic study of a large sample of normal elderly volunteers. Dementia 1994; 5:266-81.
Roth M, Tym E, Mountjoy C Q, Huppert F A, et al. CAM-DEX: A standardised instrument for the diagnosis of mental disorder in the elderly with special reference to the early detection of dementia. British Journal of Psychiatry 1986; 149:698-709.
Sachdev P S, Valenzuela M, Wang X L, Looi J C, Broadaty H.; Neurology 2002; 58: 1539-41.
Seshadri S.; J Alzheimer's Dis 2006; 9: 393-8.
Seshadri S, Wolf P A, Beiser A S, Selhub J, Au R, Jacques P F, et al.; Arch Neurol 2008; 65: 642-9.
Shipchandler M T, Moore E G. Rapid, fully automated measurement of plasma homocysteine with the Abbott IMx analyzer. Clin Chem 1995; 41:991-4.
Skoog I, Andreasson L A, Landahl S, Lernfelt B.; Hypertension 1998; 32: 404-409.
Sluimer J D, van der Flier W M, Karas G B, Fox N C, Scheltens P, Barkhof F, et al.; Radiology 2008; 248: 590-8.
Sontag E, Nunbhakdi-Craig V, Sontag J M, et al. Protein phosphatase 2A methyltransferase links homocysteine metabolism with tau and amyloid precursor protein regulation. J Neurosci 2007; 27:2751-9.

Smith A D.; Proc Natl Acad Sci USA 2002; 99: 4135-7.

Smith A D, Refsum H. Vitamin B-12 and cognition in the elderly. Am J Clin Nutr 2009; 89:7078-11S.

Smith A D.; Food Nutr Bull 2008; 29: S143-172.

Smith S M, Zhang Y, Jenkinson M, Chen J, Matthews P M, Federico A, et al.; Neuroimage 2002; 17: 479-89.

Vogiatzoglou A, Refsum H, Johnston C, Smith S M, Bradley K M, de Jager C, et al.; Neurology 2008; 71: 826-832.

Warden D R, Refsum H.; Clin Chem 2005; 51:1713-6.

Wedderburn C, Wear H, Brown J, et al. The utility of the Cambridge Behavioural Inventory in neurodegenerative disease. J Neurol Neurosurg Psychiatry 2008; 79:500-3.

Wenham P R, Price W H, Blandell G.; Lancet 1991; 337: 1158-9.

Williams J H, Pereira E A, Budge M M, Bradley K M.; Age Ageing 2002; 31: 440-4.

Wolters M. Hickstein M, Flintermann A, Tewes U, Hahn A. Cognitive performance in relation to vitamin status in healthy elderly German women—the effect of 6-month multivitamin supplementation. Prev Med 2005; 41:253-9.

Yang L K, Wong K C, Wu M Y, Liao S L, Kuo C S, Huang R F S.; J Am Coll Nutr 2007; 26: 272-278.

Yesavage J A, Brink T L, Rose T L, Lum O, Huang V, Adey M, et al.; J Psychiatr Res 1982; 17: 37-49.

Yesavage J A. Geriatric Depression Scale. Psychopharmacol Bull 1988; 24:709-11.

Zylberstein D E, Lissner L, Bjorkelund C, Mehlig K, Thelle D S, Gustafson D, et al.; Neurobiol Aging 2009; Epub ahead of print.

The invention claimed is:

1. A method for treating mild cognitive impairment (MCI) in a subject, the method comprising administering to the subject a therapeutically effective amount of folic acid, vitamin $B_6$ and vitamin $B_{12}$, wherein:
   the folic acid is administered in a daily amount of approximately 0.1 mg to approximately 1.5 mg;
   the vitamin $B_6$ is administered in a daily amount of approximately 1 mg to approximately 30 mg; and
   the vitamin $B_{12}$ is administered in a daily amount of approximately 0.01 mg to approximately 1.0 mg,
   wherein the method provides a reduction in brain atrophy by a factor of at least 2 per year compared to the absence of administration of the folic acid, vitamin $B_6$ and vitamin $B_{12}$.

2. A method for retarding the onset and/or development of MCI in a subject, the method comprising administering to the subject a therapeutically effective amount of folic acid, vitamin $B_6$ and vitamin $B_{12}$, wherein:
   the folic acid is administered in a daily amount of approximately 0.1 mg to 6 approximately 1.5 mg;
   the vitamin $B_6$ is administered in a daily amount of approximately 1 mg to approximately 30 mg; and
   the vitamin $B_{12}$ is administered in a daily amount of approximately 0.01 mg to approximately 1.0 mg,
   wherein the method provides a reduction in brain atrophy by a factor of at least 2 per year compared to the absence of administration of the folic acid, vitamin $B_6$ and vitamin $B_{12}$.

3. A method for improving cognitive function in a subject with MCI, the method comprising administering to the subject a therapeutically effective amount of folic acid, vitamin $B_6$ and vitamin $B_{12}$, wherein:
   the folic acid is administered in a daily amount of approximately 0.1 mg to approximately 1.5 mg;
   the vitamin $B_6$ is administered in a daily amount of approximately 1 mg to approximately 30 mg; and
   the vitamin $B_{12}$ is administered in a daily amount of approximately 0.01 mg to approximately 1.0 mg,
   wherein the method provides a reduction in brain atrophy by a factor of at least 2 per year compared to the absence of administration of the folic acid, vitamin $B_6$ and vitamin $B_{12}$.

4. The method of claim 1, wherein the subject is at least 60 years old.

5. The method of claim 4, wherein the subject is at least 70 years old.

6. The method of claim 2, wherein the subject is at least 50 years old.

7. The method of claim 3, wherein the subject is at least 50 years old.

8. The method of claim 1, wherein the subject is at least 50 years old.

9. The method of claim 1, which comprises administering a composition comprising the folic acid, the vitamin $B_6$ and the vitamin $B_{12}$.

10. The method of claim 2, which comprises administering a composition comprising the folic acid, the vitamin $B_6$ and the vitamin $B_{12}$.

11. The method of claim 3, which comprises administering a composition comprising the folic acid, the vitamin $B_6$ and the vitamin $B_{12}$.

12. The method of claim 1, wherein: the folic acid is administered in an amount of from approximately 0.5 mg to approximately 1.5 mg.

13. The method of claim 2, wherein: the vitamin $B_6$ is administered in an amount of approximately 15 mg to approximately 30 mg.

14. The method of claim 3, wherein: the vitamin $B_{12}$ is administered in an amount of approximately 4.0 mg to approximately 1.0 mg.

15. The method of claim 9, wherein:
   the folic acid is in an amount of approximately 0.5 mg to approximately 1.5 mg;
   the vitamin $B_6$ is in an amount of approximately 15 mg to approximately 30 mg;
   the vitamin $B_{12}$ is in an amount of approximately 0.4 mg to approximately 1.0 mg.

16. The method of claim 10:
   the folic acid is in an amount of approximately 0.5 mg to approximately 1.5 mg;
   the vitamin $B_6$ is in an amount of approximately 15 mg to approximately 30 mg;
   the vitamin $B_{12}$ is in an amount of approximately 0.4 mg to approximately 1.0 mg.

17. The method of claim 11, wherein the folic acid is in an amount of approximately 0.5 mg to approximately 1.5 mg;
   the vitamin $B_6$ is in an amount of approximately 15 mg to approximately 30 mg;
   the vitamin $B_{12}$ is in an amount of approximately 0.4 mg to approximately 1.0 mg.

18. The method of claim 1, wherein:
   attention is improved in the subject following administration of the folic acid, vitamin $B_6$ and vitamin $B_{12}$; and/or
   executive function is improved in the subject following administration of the folic acid, vitamin $B_6$ and vitamin $B_{12}$; and/or
   learning or memory is improved in the subject following administration of the folic acid, vitamin $B_6$ and vitamin $B_{12}$.

19. The method of claim 2, wherein:
attention is improved in the subject following administration of the folic acid, vitamin $B_6$ and vitamin $B_{12}$; and/or
executive function is improved in the subject following administration of the folic acid, vitamin $B_6$ and vitamin $B_{12}$; and/or
learning or memory is improved in the subject following administration of the folic acid, vitamin $B_6$ and vitamin $B_{12}$.

20. The method of claim 3, wherein:
attention is improved in the subject following administration of the folic acid, vitamin $B_6$ and vitamin $B_{12}$; and/or
executive function is improved in the subject following administration of the folic acid, vitamin $B_6$ and vitamin $B_{12}$; and/or
learning or memory is improved in the subject following administration of the folic acid, vitamin $B_6$ and vitamin $B_{12}$ memory is improved in the subject following administration of the at least one agent.

21. The method of claim 1, wherein the subject has a baseline tHcy exceeding approximately 9.5 µmol/L.

22. The method of claim 1, wherein the vitamin $B_{12}$ is as cyanocobalamin, methylcobalamin, hydroxocobalamin or adenosylcobalamin or a salt thereof; and/or wherein the folic acid is as 5-methyltetrahydrofolate, 5,10-methylenetetrahydrofolate, 5,10-methenyltetrahydrofolate, 5,10-formiminotetrahydrofolate, 5-formyltetrahydrofolate (leucovorin) or 10-formyltetrahydrofolate or a salt thereof or is as a salt of folic acid; and/or wherein the vitamin $B_6$ is as pyridoxine or a salt thereof.

23. A method which comprises administering to a subject a therapeutically effective amount of at least one agent which reduces brain atrophy, the method being selected from:
(i) a method for treating mild cognitive impairment (MCI) in the subject;
(ii) a method for retarding the onset and/or development of MCI in the subject;
(iii) a method for improving cognitive function in the subject, wherein the subject has MCI,
wherein the method comprises administering a dosage form which comprises approximately 0.1 mg to approximately 1.5 mg of folic acid, approximately 1 mg to approximately 30 mg vitamin $B_6$ and approximately 0.01 mg to approximately 1.0 mg of vitamin $B_{12}$, and wherein the method provides a reduction in brain atrophy by a factor of at least 2 per year compared to the absence of administration of the folic acid, vitamin $B_6$ and vitamin $B_{12}$.

24. The method of claim 23, wherein the subject's level of baseline tHcy exceeds 9.5 µmol/L.

25. The method of claim 23 wherein the vitamin $B_{12}$ is as cyanocobalamin, methylcobalamin, hydroxocobalamin or adenosylcobalamin or a salt thereof, and/or wherein the folic acid is as 5-methyltetrahydrofolate, 5,10-methylenetetrahydrofolate, 5,10-methenyltetrahydrofolate, 5,10-formiminotetrahydrofolate, 5-formyltetrahydrofolate (leucovorin) or 10-formyltetrahydrofolate or a salt thereof.

26. The method of claim 1, wherein the subject is at least 50 years old.

27. The method of claim 1 wherein the subject is administered the folic acid, vitamin $B_6$ and vitamin $B_{12}$ for a minimum of 18 months.

28. The method of claim 2 wherein the subject is administered the folic acid, vitamin $B_6$ and vitamin $B_{12}$ for a minimum of 18 months.

29. The method of claim 3 wherein the subject is administered the folic acid, vitamin $B_6$ and vitamin $B_{12}$ for a minimum of 18 months.

30. The method of claim 2 wherein the subject has a baseline tHcy exceeding above about 9.5 µmol/L.

31. The method of claim 3 wherein the subject has a baseline tHcy exceeding above about 9.5 µmol/L.

32. A method for retarding the onset and/or development of MCI in a subject or for improving cognitive function in a subject with MCI, the method comprising administering to the subject for a minimum of 18 months a therapeutically effective amount of folic acid, vitamin $B_6$ and vitamin $B_{12}$, wherein:
the folic acid is in an amount of approximately 0.5 mg to approximately 1.5 mg;
the vitamin $B_6$ is in an amount of approximately 15 mg to approximately 30 mg; and
the vitamin $B_{12}$ is in an amount of approximately 0.4 mg to approximately 1.0 mg,
wherein the method provides a reduction in brain atrophy by a factor of at least 2 per year compared to the absence of administration of the folic acid, vitamin $B_6$ and vitamin $B_{12}$.

33. The method of claim 32, wherein the folic acid, vitamin $B_6$ and vitamin $B_{12}$ are administered at least once a day for the minimum period of at least 18 months.

34. The method of claim 32, wherein the folic acid, vitamin $B_6$ and vitamin $B_{12}$ are administered at least once a day for a minimum period of at least 24 months.

35. The method of claim 32, wherein the vitamin $B_{12}$ is as cyanocobalamin, methylcobalamin, hydroxocobalamin or adenosylcobalamin or a salt thereof; and/or wherein the folic acid is as 5-methyltetrahydrofolate, 5,10-methylenetetrahydrofolate, 5,10-methenyltetrahydrofolate, 5,10-formiminotetrahydrofolate, 5-formyltetrahydrofolate (leucovorin) or 10-formyltetrahydrofolate or a salt thereof or is as a salt of folic acid; and/or wherein the vitamin $B_6$ is as pyridoxine or a salt thereof.

36. The method of claim 32, wherein:
attention is improved in the subject following administration of the folic acid, vitamin $B_6$ and vitamin $B_{12}$; and/or
executive function is improved in the subject following administration of the folic acid, vitamin $B_6$ and vitamin $B_{12}$; and/or
learning or memory is improved in the subject following administration of the folic acid, vitamin $B_6$ and vitamin $B_{12}$.

37. The method of claim 33 wherein the subject is administered the folic acid, vitamin $B_6$ and vitamin $B_{12}$ for a minimum of 18 months and has a baseline tHcy exceeding about 13 µmol/L.

38. The method of claim 1 wherein the subject is administered the folic acid, vitamin $B_6$ and vitamin $B_{12}$ for a minimum of 18 months and has a baseline tHcy exceeding about 13 µmol/L.

39. The method of claim 2 wherein the subject is administered the folic acid, vitamin $B_6$ and vitamin $B_{12}$ for a minimum of 18 months and has a baseline tHcy exceeding about 13 µmol/L.

40. The method of claim 3 wherein the subject is administered the folic acid, vitamin $B_6$ and vitamin $B_{12}$ for a minimum of 18 months and has a baseline tHcy exceeding about 13 µmol/L.

41. The method of claim 1, wherein the folic acid is administered in a daily amount of approximately 0.8 mg, the vitamin $B_6$ is administered in a daily amount of approximately 20 mg and the vitamin $B_{12}$ is administered in a daily amount of approximately 0.5 mg.

42. A method of reducing brain atrophy, wherein the method consists essentially of administering to a subject a therapeutically effective amount of the following:
   (a) folic acid in an amount of approximately 0.1 mg to approximately 1.5 mg;
   (b) vitamin $B_6$ in an amount of approximately 1 mg to approximately 30 mg; and
   (c) vitamin $B_{12}$ in an amount of approximately 0.01 mg to approximately 1.0 mg, wherein the method provides a reduction in brain atrophy by a factor of at least 2 compared to the absence of administration of the folic acid, vitamin $B_6$ and vitamin $B_{12}$.

* * * * *